United States Patent
Matsuura

(10) Patent No.: US 12,112,476 B2
(45) Date of Patent: Oct. 8, 2024

(54) MEDICAL SUPPORT DEVICE, OPERATION METHOD OF MEDICAL SUPPORT DEVICE, NON-TRANSITORY COMPUTER READABLE MEDIUM, AND MEDICAL SUPPORT SYSTEM

(71) Applicant: FUJIFILM Corporation, Tokyo (JP)

(72) Inventor: Naoki Matsuura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 323 days.

(21) Appl. No.: 17/674,818

(22) Filed: Feb. 17, 2022

(65) Prior Publication Data

US 2022/0172366 A1 Jun. 2, 2022

Related U.S. Application Data

(63) Continuation of application No. PCT/JP2020/031012, filed on Aug. 17, 2020.

(30) Foreign Application Priority Data

Aug. 19, 2019 (JP) ................................. 2019-150031

(51) Int. Cl.
*G06T 7/00* (2017.01)
*G06T 7/70* (2017.01)
(Continued)

(52) U.S. Cl.
CPC .............. *G06T 7/0012* (2013.01); *G06T 7/70* (2017.01); *G06V 10/764* (2022.01);
(Continued)

(58) Field of Classification Search
CPC .................... G06T 7/0012; G06T 7/70; G06T 2007/30004; G06V 10/764; G06V 2201/03
See application file for complete search history.

(56) References Cited

U.S. PATENT DOCUMENTS 6,845,213 B2 * 1/2005 Maas .................. G06V 20/635
386/E5.052
10,572,994 B2 2/2020 Katsumata
(Continued)

FOREIGN PATENT DOCUMENTS

JP 2014531570 11/2014
JP 2015038441 2/2015
(Continued)

OTHER PUBLICATIONS

Office Action of Japan Counterpart Application, with English translation thereof, issued on Dec. 6, 2022, pp. 1-9.
(Continued)

*Primary Examiner* — Kevin Ky
(74) *Attorney, Agent, or Firm* — JCIPRNET

(57) ABSTRACT

A medical support device includes a processor, in which the processor acquires a medical image, acquires correspondence information in which the medical image is associated in advance with presence or absence of a foreign substance image included in the medical image, generates foreign substance estimation information obtained by estimating the presence or absence of the foreign substance image included in the medical image based on the medical image and the correspondence information, and controls a notification based on the foreign substance estimation information.

15 Claims, 15 Drawing Sheets

(51) Int. Cl.
*G06V 10/764* (2022.01)
*G08B 21/18* (2006.01)

(52) U.S. Cl.
CPC ............... *G06T 2207/30004* (2013.01); *G06V 2201/03* (2022.01); *G08B 21/18* (2013.01)

(56) References Cited

U.S. PATENT DOCUMENTS

| | | | |
|---|---|---|---|
| 2006/0103850 A1* | 5/2006 | Alphonse | A61B 5/0066 356/479 |
| 2013/0136323 A1 | 5/2013 | Asiyanbola et al. | |
| 2013/0279750 A1* | 10/2013 | Zhou | G06T 7/001 382/103 |
| 2014/0086390 A1 | 3/2014 | Nakatsugawa et al. | |
| 2014/0376782 A1* | 12/2014 | Li | G06T 7/0004 382/110 |
| 2015/0018671 A1 | 1/2015 | Marentis et al. | |
| 2015/0087522 A1* | 3/2015 | Kawaguchi | H01Q 21/0006 343/872 |
| 2015/0141806 A1* | 5/2015 | Smith | A61B 5/062 600/424 |
| 2017/0069081 A1 | 3/2017 | Gluncic et al. | |
| 2017/0307551 A1* | 10/2017 | Murakami | G01N 21/3103 |
| 2018/0209922 A1 | 7/2018 | Yamakawa et al. | |
| 2019/0130561 A1 | 5/2019 | Katsuhara et al. | |
| 2019/0150857 A1 | 5/2019 | Nye et al. | |
| 2019/0183451 A1* | 6/2019 | Yu | G06F 16/50 |
| 2020/0300784 A1* | 9/2020 | Ohbayashi | G01N 23/083 |
| 2021/0015433 A1 | 1/2021 | Nye et al. | |

FOREIGN PATENT DOCUMENTS

| | | |
|---|---|---|
| JP | 2018021817 | 2/2018 |
| JP | 2018130336 | 8/2018 |
| JP | 2019080906 | 5/2019 |
| JP | 2019093137 | 6/2019 |
| WO | 2012164901 | 12/2012 |
| WO | 2013009709 | 1/2013 |
| WO | 2016037160 | 3/2016 |
| WO | 2016171186 | 10/2016 |

OTHER PUBLICATIONS

"Decision of Refusal of Japan Counterpart Application", issued on Feb. 21, 2023, with English translation thereof, p. 1-p. 6.
"Office Action of Europe Counterpart Application", issued on Dec. 7, 2023, pp. 1-3.
Shinobu Sugishita et al., "Examination and countermeasure for preventing retained surgical items" with English Abstract, Journal of Japan Association of Radiological Technologists, vol. 64, 2017, pp. 20-27.
"International Search Report (Form PCT/ISA/210) of PCT/JP2020/031012," mailed on Sep. 29, 2020, with English translation thereof, pp. 1-6.
"Written Opinion of the International Searching Authority (Form PCT/ISA/237)" of PCT/JP2020/031012, mailed on Sep. 29, 2020, with English translation thereof, pp. 1-8.
"Search Report of Europe Counterpart Application", issued on Jul. 15, 2022, p. 1-p. 9.
"Notice of Reasons for Refusal of Japan Counterpart Application", issued on Jul. 2, 2024, with English translation thereof, pp. 1-31.

* cited by examiner

FIG. 4

| MEDICAL IMAGE | PRESENCE OR ABSENCE OF FOREIGN SUBSTANCE | TYPE OF FOREIGN SUBSTANCE |
|---|---|---|
| 66a | ABSENCE | - |
| 66b | PRESENCE | METALLIC NECKLACE |
| 66c | PRESENCE | IMPLANTABLE DEVICE, MANUFACTURED BY ABC, MODEL: X-111 |
| 66d | PRESENCE | FOREIGN SUBSTANCE IN ESOPHAGUS, BUTTON BATTERY |
| 66e | PRESENCE | SURGICAL RESIDUAL FOREIGN SUBSTANCE, GAUZE |

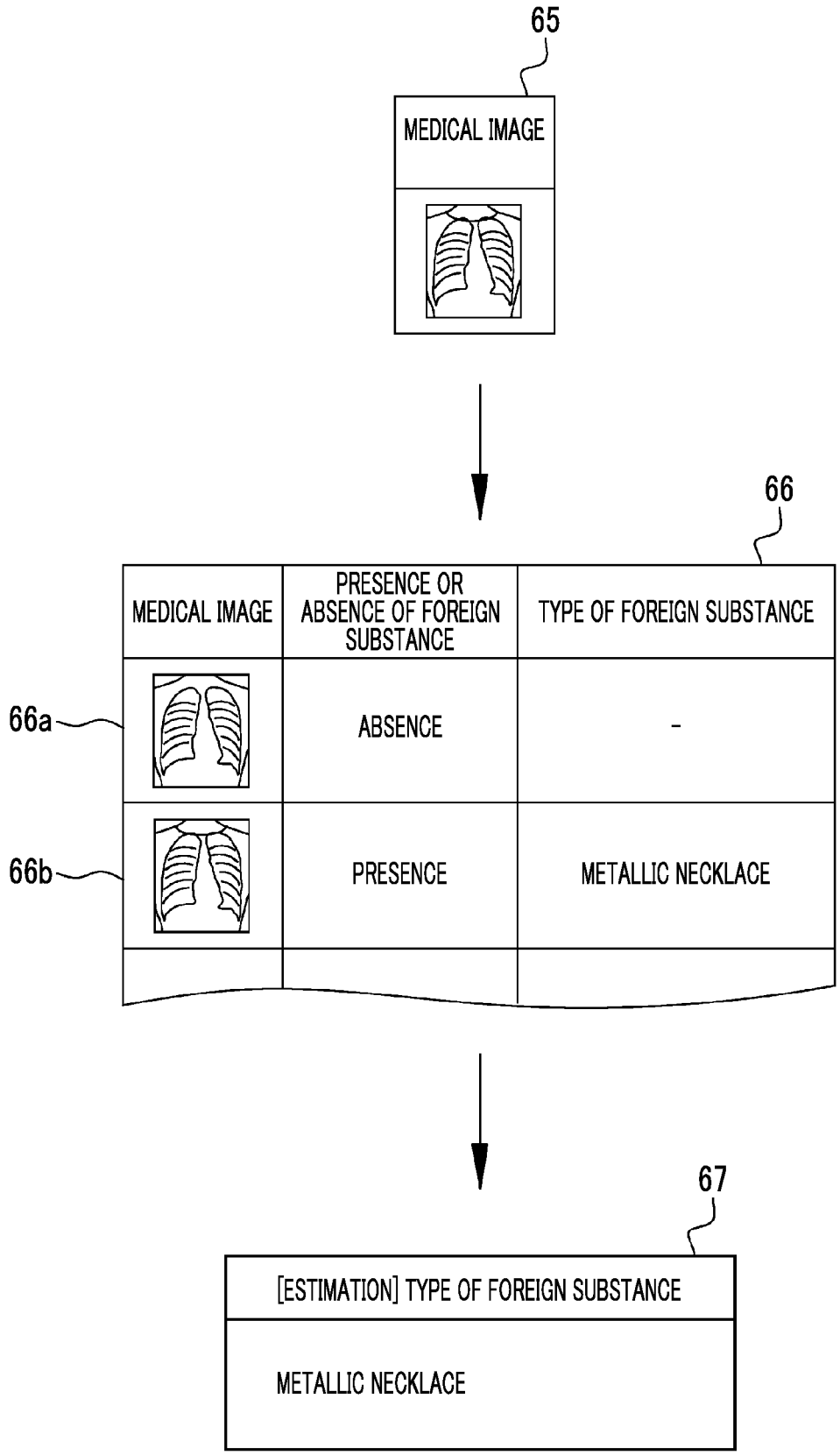

FIG. 6

| MEDICAL IMAGE | PRESENCE OR ABSENCE OF FOREIGN SUBSTANCE | TYPE OF FOREIGN SUBSTANCE | POSITION OF FOREIGN SUBSTANCE |
|---|---|---|---|
| 66a  | ABSENCE | - | - |
| 66b 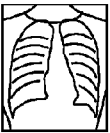 | PRESENCE | METALLIC NECKLACE | NECK, OUTSIDE BODY |
| 66c  | PRESENCE | IMPLANTABLE DEVICE, MANUFACTURED BY ABC, MODEL: X-111 | IN FRONT OF LEFT SHOULDER, BENEATH SKIN |
| 66d  | PRESENCE | FOREIGN SUBSTANCE IN ESOPHAGUS, BUTTON BATTERY | ESOPHAGUS, CENTER |
| 66e 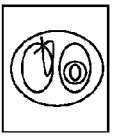 | PRESENCE | SURGICAL RESIDUAL FOREIGN SUBSTANCE, GAUZE | DIAPHRAGM, LOWER RIGHT |

71

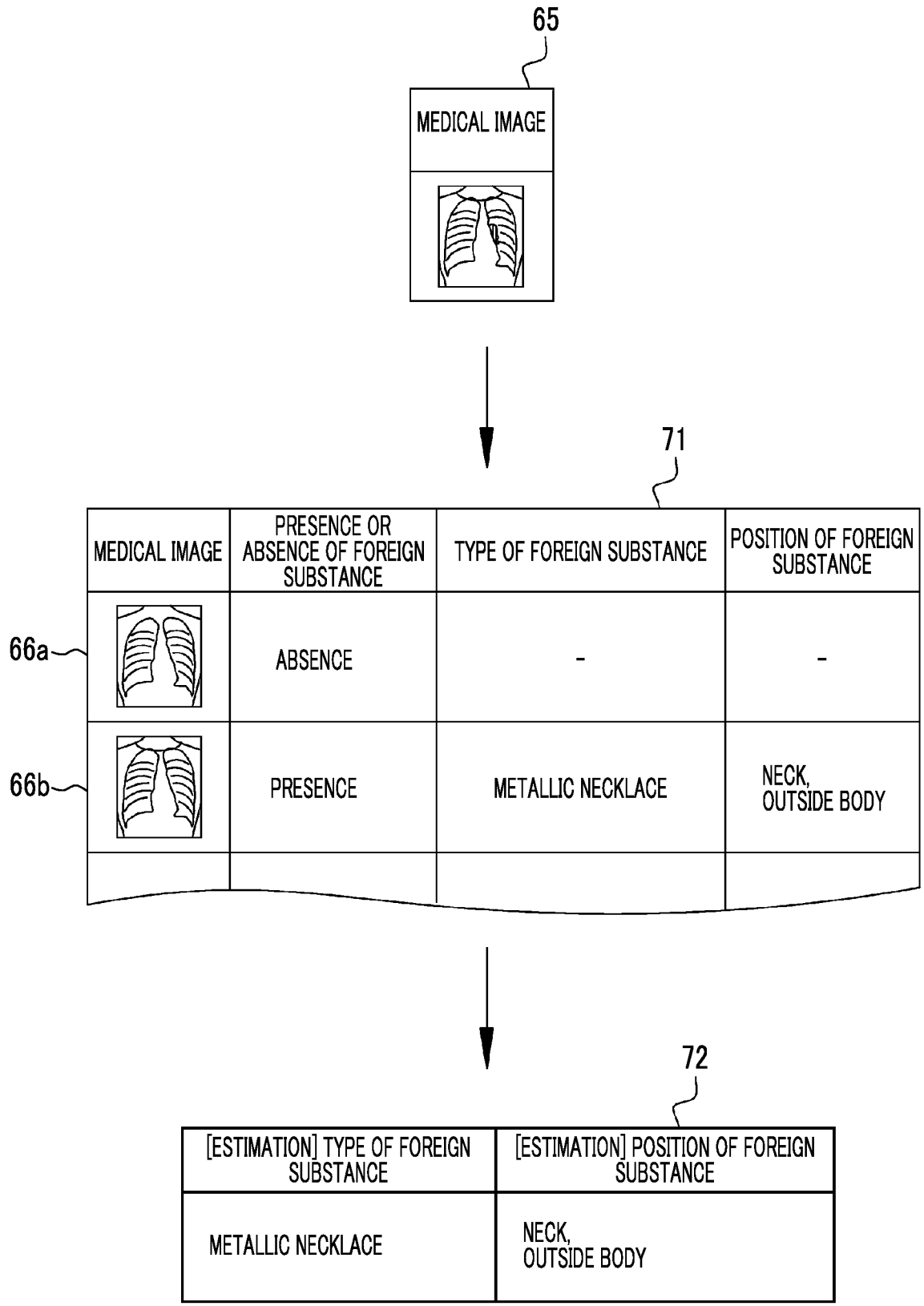

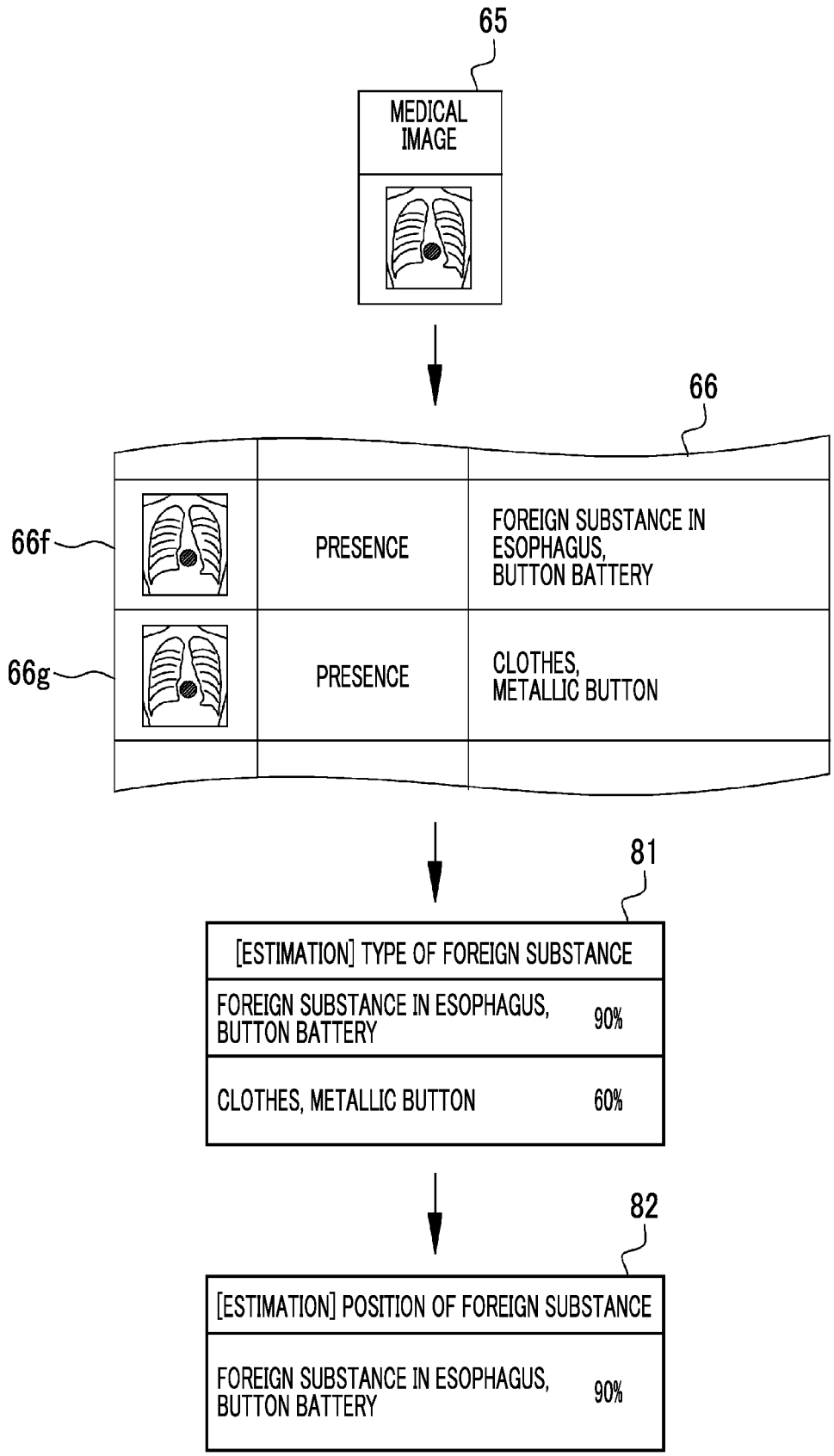

FIG. 14

| MEDICAL IMAGE | PRESENCE OR ABSENCE OF FOREIGN SUBSTANCE | TYPE OF FOREIGN SUBSTANCE | POSITION OF FOREIGN SUBSTANCE | MEASURE INFORMATION |
|---|---|---|---|---|
| 66a | ABSENCE | - | - | - |
| 66b | PRESENCE | METALLIC NECKLACE | NECK, OUTSIDE BODY | PA2: 31 JULY, 2019, ABNORMAL, IMAGING FAILURE, RE-IMAGING (NECKLACE REMOVAL) |
| 66c | PRESENCE | IMPLANTABLE DEVICE, MANUFACTURED BY ABC, MODEL: X-111 | IN FRONT OF LEFT SHOULDER, BENEATH SKIN | PA1: 30 JULY, 2019, NORMAL |

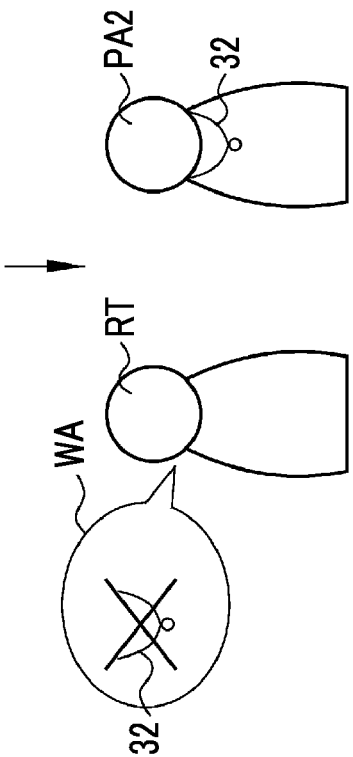

MEDICAL SUPPORT DEVICE, OPERATION METHOD OF MEDICAL SUPPORT DEVICE, NON-TRANSITORY COMPUTER READABLE MEDIUM, AND MEDICAL SUPPORT SYSTEM

CROSS-REFERENCE TO RELATED APPLICATIONS

This application is a Continuation of PCT International Application No. PCT/JP2020/031012 filed on 17 Aug. 2020, which claims priority under 35 U.S.C § 119(a) to Japanese Patent Application No. 2019-150031 filed on 19 Aug. 2019. The above application is hereby expressly incorporated by reference, in its entirety, into the present application.

BACKGROUND OF THE INVENTION

1. Field of the Invention

The present invention relates to a medical support device, an operation method of a medical support device, a non-transitory computer readable medium, and a medical support system.

2. Description of the Related Art

In a medical field, it is important to prevent an accident that is a medical accident or an incident that is a case having a risk of occurrence of the medical accident. One of the causes of the incident or the accident in diagnosis using a medical image is a residual foreign substance at the time of imaging. The residual foreign substance present on a subject generates a medical image having insufficient image quality that hinders interpretation, leading to deterioration of diagnostic ability. In addition, residual foreign substance generated during surgery leads to damage to a patient, and also leads to many problems in a medical facility, such as cause analysis, examination of recurrence prevention measures, or litigation risk, and thus early detection is necessary.

As an apparatus that detects a foreign substance present inside an object including a human body, an X-ray examination apparatus that creates a tomographic image from a frame data of a plurality of tomographic planes and detects a foreign substance by a three-dimensional distribution of edge information computed from the tomographic image is disclosed (WO2015/111728A, corresponding to US2016/0349192A1). In addition, a medical image diagnostic device that detects a site and presents warning information or the like in a case in which there is a foreign substance, such as metal in a body is disclosed (JP2017-202315A).

SUMMARY OF THE INVENTION

In interpretation of a medical image, it is necessary for an interpreter to be proficient in determining a lesion, a foreign substance, or the like. In addition, due to the nature of medical treatment, it is difficult to use an interpretation result by image processing or the like with an apparatus or the like as a diagnostic result as it is. Further, even in a case in which the foreign substance is detected by the interpretation, there are a foreign substance that requires a measure and a foreign substance that does not require a measure, so it is necessary to further determine a measure for the foreign substance. For example, in a case of a magnetic treatment device that is forgotten to be removed at the time of imaging of an X-ray image, removal and re-imaging are required, and thus the magnetic treatment device is a foreign substance that requires a measure, such as removal of the foreign substance and re-imaging after an original image is regarded as imaging failure. In addition, in a case of a foreign substance image by a pacemaker detected in the medical image, removal and re-imaging are not required, it is a foreign substance that does not require a measure. Therefore, in addition to detection of the foreign substance, it is important to correctly determine a type of the foreign substance in order to prevent the incident or the accident and to improve the efficiency of a medical work.

The present invention is to provide a medical support device, an operation method of a medical support device, a non-transitory computer readable medium, and a medical support system that can support a medical staff to appropriately determine the presence or absence of a foreign substance image included in a medical image and a type of a foreign substance that forms the foreign substance image.

An aspect of the present invention relates to a medical support device comprising a processor. The processor acquires a medical image including a subject image, acquires correspondence information in which the medical image is associated in advance with presence or absence of a foreign substance image included in the medical image and a type of a foreign substance that forms the foreign substance image in a case in which the foreign substance image is present, generates foreign substance estimation information obtained by estimating the presence or absence of the foreign substance image included in the medical image, and the type of the foreign substance that forms the foreign substance image in a case in which the foreign substance image is present based on the medical image and the correspondence information, and controls a notification based on the foreign substance estimation information.

It is preferable that the processor acquire the correspondence information in which the medical image is associated in advance with a position of the foreign substance, and generate the foreign substance estimation information obtained by estimating the position of the foreign substance based on the medical image and the correspondence information.

It is preferable that the processor acquire measure information regarding a measure corresponding to the medical image based on the notification, and the medical support device further comprises a database that stores measure correspondence information in which the medical image is associated with the measure information.

It is preferable that the processor control the notification based on the measure correspondence information.

It is preferable that the processor acquire imaging instruction information for acquiring the medical image, and control the notification based on the imaging instruction information and/or the measure correspondence information regarding the medical image in a case in which the medical image including the subject image based on the imaging instruction information is acquired again.

It is preferable that the notification be performed by at least one of image display, sound output, or vibration generation.

It is preferable that the notification be performed with respect to a person other than a patient having a subject that forms the subject image.

It is preferable that the processor perform a guide with respect to a patient having a subject based on the foreign substance estimation information.

It is preferable that the guide include the type of the foreign substance.

It is preferable that the processor change a content of the guide depending on the type of the foreign substance.

It is preferable that the processor generate imaging failure determination information obtained by determining whether or not the medical image is imaging-failed based on the foreign substance estimation information.

It is preferable that the processor generate imaging instruction information based on the foreign substance estimation information.

In addition, another aspect of the present invention relates to a medical support system comprising any medical support device according to the above.

It is preferable that the medical support system further comprise a small portable terminal having a function of giving the notification, in which the processor gives the notification by the small portable terminal.

In addition, still another aspect of the present invention relates to an operation method of a medical support device, the method comprising an image acquisition step of acquiring a medical image including a subject image, an correspondence information acquisition step of acquiring correspondence information in which the medical image is associated in advance with presence or absence of a foreign substance image included in the medical image and a type of a foreign substance that forms the foreign substance image in a case in which the foreign substance image is present, a foreign substance estimation information generation step of generating foreign substance estimation information obtained by estimating the presence or absence of the foreign substance image included in the medical image, and the type of the foreign substance that forms the foreign substance image in a case in which the foreign substance image is present based on the medical image and the correspondence information, and a notification control step of controlling a notification based on the foreign substance estimation information.

In addition, still another aspect of the present invention relates to a non-transitory computer readable medium for storing a computer-executable program causing a computer to function as a medical support device. The computer-executable program causes the computer to execute an image acquisition step of acquiring a medical image including a subject image, an correspondence information acquisition step of acquiring correspondence information in which the medical image is associated in advance with presence or absence of a foreign substance image included in the medical image and a type of a foreign substance that forms the foreign substance image in a case in which the foreign substance image is present, a foreign substance estimation information generation step of generating foreign substance estimation information obtained by estimating the presence or absence of the foreign substance image included in the medical image, and the type of the foreign substance that forms the foreign substance image in a case in which the foreign substance image is present based on the medical image and the correspondence information, and a notification control step of controlling a notification based on the foreign substance estimation information.

According to the present invention, it is possible to support a medical staff to appropriately determine the presence or absence of the foreign substance image included in the medical image and the type of the foreign substance that forms the foreign substance image.

BRIEF DESCRIPTION OF THE DRAWINGS

FIG. 4 is an explanatory diagram for describing correspondence information.

FIG. 5 is an explanatory diagram for describing a flow of estimation of a type of a foreign substance and the like by a foreign substance estimation unit.

FIG. 6 is an explanatory diagram for describing the correspondence information including a position of the foreign substance.

FIG. 7 is an explanatory diagram for describing a flow of estimation of the position of a foreign substance and the like by the foreign substance estimation unit.

FIG. 8 is an explanatory diagram for describing a flow of estimation of the type of the foreign substance by imparting an adaptation degree by the foreign substance estimation unit.

FIG. 11 is a block diagram showing a function of the medical support device comprising an imaging failure determination unit and the like.

FIG. 12 is a block diagram showing a function of the medical support device comprising an imaging instruction information acquisition unit and the like.

FIG. 14 is an explanatory diagram for describing use of the measure information.

DESCRIPTION OF THE PREFERRED EMBODIMENTS

A medical support device according to an embodiment of the present invention is used in a scene in which a medical staff acquires or interprets a medical image. The medical staff is a medical staff who is involved in the medical image, for example, a radiologist who acquires the medical image, an interpreter who interprets the medical image, or a nurse or a clinical technologist who is involved in the medical image in response to an instruction of a doctor. The medical support device is installed in an image examination room, a medical examination room, or the like, and in the present embodiment, the medical support device is installed in an operation room of the image examination room. The medical support device is, for example, a computer, such as a personal computer, in which an application program for executing a predetermined function is installed.

Figure 1:
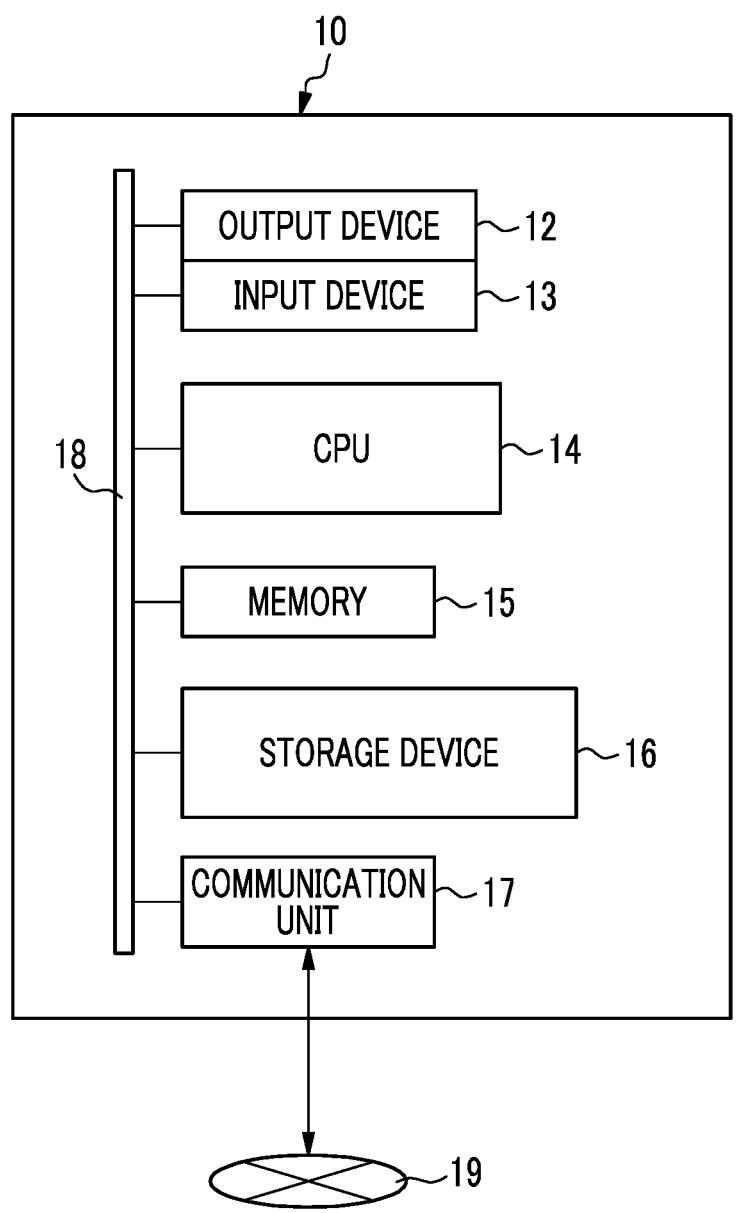
FIG. 1 is a block diagram showing a configuration of a medical support device.

As shown in FIG. 1, a medical support device 10 comprises a central processing unit (CPU) 14 which is a processor, a memory 15, and a storage device 16, and a communication unit 17, in addition to an output device 12, such as a display, and an input device 13, such as a mouse, a microphone, or a keyboard. These units are mutually connected via a data bus 18. The communication unit 17 has a function of communicating with another device or a network 19.

The storage device 16 is a hard disk drive which is built in the medical support device 10 or connected to the medical support device 10 via a cable or the network 19, or a disk array in which a plurality of hard disk drives are mounted. Therefore, the storage device 16 functions as a storage unit. The storage device 16 stores a control program, such as an operating system, various application programs, various data associated with these programs, a database, and the like.

The memory 15 is a work memory for the CPU 14 to execute a process. The CPU 14 comprehensively controls each unit of the medical support device 10 by loading the program stored in the storage device 16 into the memory 15 and executing the process according to the program.

The medical support device 10 may be connected to, via the communication unit 17, an information management server, such as a hospital information system (HIS), a radiology information system (RIS), and the like, which registers and manages information, such as patient information, medical care information, examination information, accounting information, and imaging instruction for image diagnosis, for each patient or an image server, such as a picture archiving and communication system for medical application (PACS), which manages a captured medical image and information regarding the medical image. In a case in which the medical support device 10 is mutually connected to these servers, mutual communication of various pieces of information is performed with these servers. In addition, a computer of the medical support device 10 can also be used as a client terminal of these servers.

Figure 2:
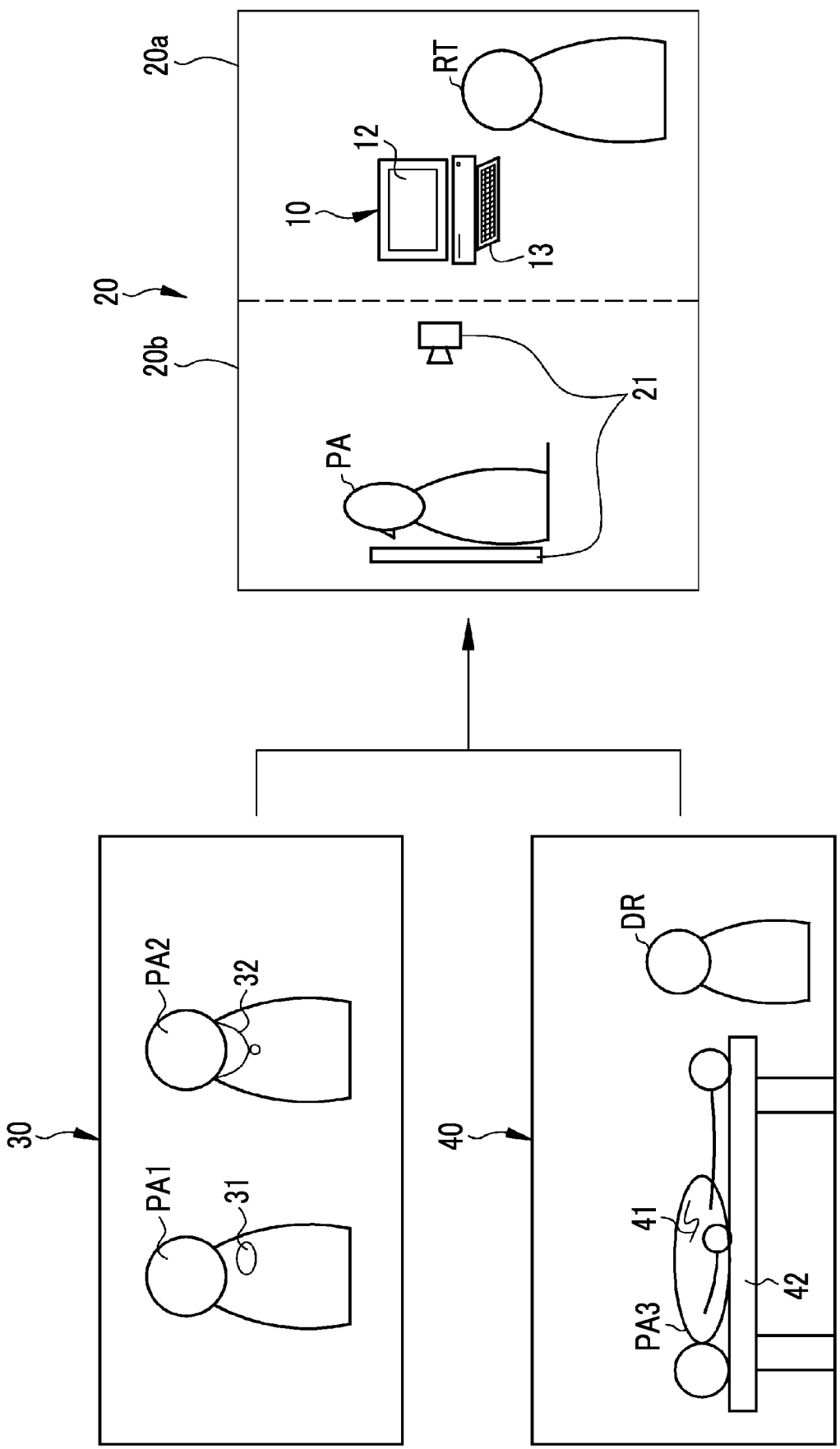
FIG. 2 is an explanatory diagram for describing a flow of medical image acquisition.

As shown in FIG. 2, in the present embodiment, the medical support device 10 is installed in an operation room 20a of an image examination room 20, and is operated by a person in charge of interpretation of the medical image, such as a radiologist RT. The image examination room 20 includes the operation room 20a and an examination room 20b. For example, an X-ray imaging apparatus 21 is installed in the examination room 20b, and imaging is performed with respect to a patient PA.

Examples of a target person for medical image acquisition include a patient PA1 or a patient PA2 who visit a medical examination. The patient PA1 or the patient PA2 has the medical examination other than an image examination in a medical examination room 30, and then has the image examination in the image examination room 20. In addition, examples of the target person for medical image acquisition include a patient PA3 who has a surgery by a doctor DR in a surgery room 40 comprising a surgery table 42. The patient PA3 has the image examination for confirming a postoperative condition by the image examination. Note that the patient PA is a general term for the patients. Therefore, the patient PA includes the patient PA1, the patient PA2, and the patient PA3.

For example, the patient PA1 who has the examination subcutaneously wears a pacemaker, which is an implantable device. This pacemaker is defined as a foreign substance 31. In addition, the patient PA2 who has the examination has the examination while wearing a foreign substance 32 which is a metallic necklace. In addition, the patient PA3 who has the surgery has terminated the surgery with the gauze that can be detected by X-rays in a body, and has a foreign substance 41 that is the gauze. The foreign substance 31 and the foreign substance 41 cannot be confirmed from the outside in a case in which the medical image is acquired. In addition, the foreign substance 32 may not be able to be confirmed from the outside in a case in which the medical image is acquired due to examination clothes or the like.

For example, X-ray imaging is performed with respect to the patient PA1 having the foreign substance 31, the patient PA2 having the foreign substance 32, and the patient PA3 having the foreign substance 41 in the image examination room 20 or the like. The radiologist RT acquires each of the medical images by using the X-ray imaging apparatus 21 with respect to the patient PA1 having the foreign substance 31, the patient PA2 having the foreign substance 32, and the patient PA3 having the foreign substance 41 in a state of being not aware of the foreign substance 31, the foreign substance 32, and the foreign substance 41, for example, in response to an imaging instruction shown on a display of the medical support device 10 that also serves as a console of the RIS (not shown). The medical image acquired by the imaging is displayed on the display of the medical support device 10 in order for the radiologist RT to determine an imaging failure and acquire a successful medical image in response to the imaging instruction.

Figure 3:
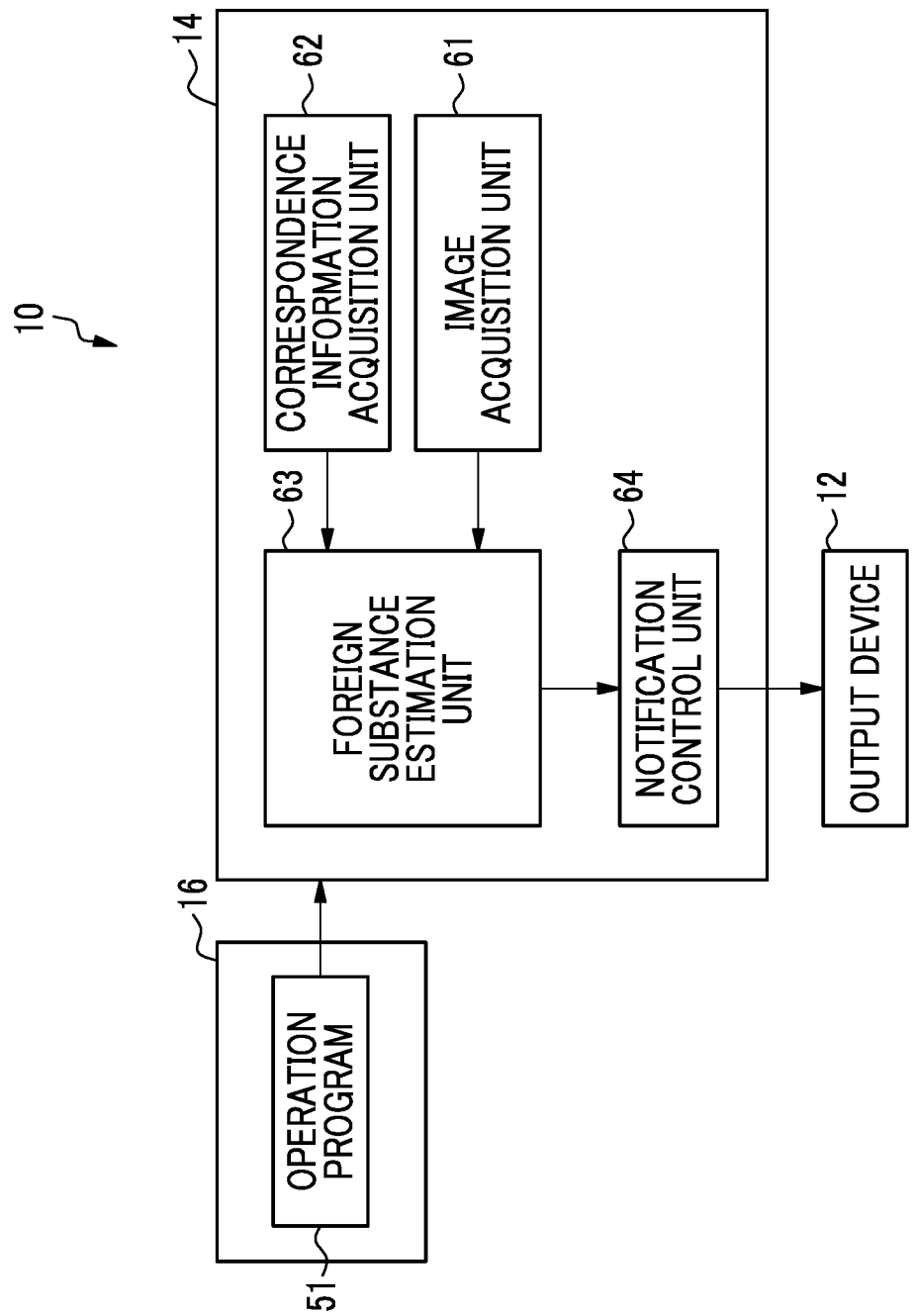
FIG. 3 is a block diagram showing a function of the medical support device.

As shown in FIG. 3, in the medical support device 10, an operation program 51 is stored in the storage device 16. By the activation of the operation program 51, the CPU 14, which is a processor, cooperates with the memory 15 and the like to function as an image acquisition unit 61, a correspondence information acquisition unit 62, a foreign substance estimation unit 63, a notification control unit 64, an imaging failure determination unit 98, and a measure information acquisition unit 101 (see FIG. 12), an imaging instruction information generation unit 99, an imaging instruction information acquisition unit 105 (see FIG. 12), and the like. Therefore, the medical support device 10 comprises the image acquisition unit 61, the correspondence information acquisition unit 62, the foreign substance estimation unit 63, the notification control unit 64, the imaging failure determination unit 98, the measure information acquisition unit 101, the imaging instruction information generation unit 99, the imaging instruction information acquisition unit 105, and the like.

The image acquisition unit 61 acquires the captured medical image. Since the medical image is captured for the patient PA as a target, the medical image includes a part or all of the body of the patient PA and, in some cases, a subject image with the foreign substance as a subject. Therefore, in some cases, the subject image may include a foreign substance image. The correspondence information acquisition unit 62 acquires correspondence information in which the medical image is associated in advance with the presence or absence of the foreign substance image included in the medical image and a type of the foreign substance that forms the foreign substance image in a case in which the foreign substance image is present. As the correspondence information, for example, the information stored in the storage device 16 is used. The foreign substance estimation unit 63 acquires the medical image from the image acquisition unit 61, and acquires the correspondence information from the correspondence information acquisition unit 62. The foreign substance estimation unit 63 generates foreign substance estimation information obtained by estimating the presence or absence of the foreign substance image included in the medical image and the type of the foreign substance that forms the foreign substance image in a case in which the foreign substance image is present based on the medical image and the correspondence information. The notification control unit 64 acquires the generated foreign substance estimation information. The notification control unit 64 controls a notification based on the foreign substance estimation information acquired from the foreign substance estimation unit 63. In a case in which the notification is given, the notification is given using the output device 12 or the like, such as a display.

Next, each unit and the like provided in the medical support device 10 will be described in detail. First, the medical image acquired by the image acquisition unit 61 is the medical image acquired for diagnosis, examination, or the like, and is captured by various modalities. Examples of the medical image include images mainly handled by a radiology department, such as an X-ray image by computed radiography (CR), a so-called computed tomography (CT) image by CT, a mammography image by mammography (MG), and a so-called magnetic resonance imaging (MRI) image by MRI. The medical image need only be any image data that can be processed by the computer.

In the present embodiment, the medical image is image data conforming to a digital imaging and communications in medicine (DICOM) standard. Since the DICOM standard, which is a standard for the medical image, is followed, mutual communication related to the medical image and information incidental to the medical image is possible between devices inside and outside a diagnosis facility that handles the medical image. Since the medical support device 10 also serves as the console of the RIS, it is possible to transmit and receive the medical image and the information incidental to the medical image to and from the RIS by using the computer which is the medical support device 10. For example, the patient information is incidental to the imaging instruction information transmitted to the console by the RIS, and in response to this imaging instruction information, for example, the patient information is incidental to the X-ray image acquired by imaging with the X-ray imaging apparatus 21. Therefore, the acquired X-ray image, which is the medical image, is the X-ray image according to the DICOM to which the imaging instruction information and/or the patient information are incidental. The acquired X-ray image is acquired by the image acquisition unit 61 and is transmitted to a server of the RIS after imaging. In addition, the acquired X-ray image is displayed on the medical support device 10 such that the radiologist RT determines the imaging failure and acquires the successful medical image in response to the imaging instruction.

The correspondence information acquisition unit 62 acquires the correspondence information in which the medical image is associated in advance with the presence or absence of the foreign substance image included in the medical image. Note that in a case in which the foreign substance image is present in the medical image, the correspondence information in which the medical image is associated with the type of the foreign substance that forms the foreign substance image is further acquired. The foreign substance that forms the foreign substance image refers to a substance that is included in the image of the patient PA or the like in the medical image but is not derived from a living body, such as the patient PA, which is the target of the medical image. Therefore, for example, a lesion and the like of the patient PA are not included in the foreign substance. In addition, for example, a shadow formed by the imaging apparatus or the image processing is not included in the foreign substance.

Examples of the foreign substance which is not derived from the living body, such as the patient PA, which is the target of imaging but is included in the patient PA include a foreign substance present in the body of the patient PA and a foreign substance present outside the body of the patient PA. Among the substances in the body, examples of the foreign substance that requires a measure include residual (left) foreign substance present in the body during the surgery, such as gauze, forcep (pean), needle, or various plugs, a foreign substance, such as residual glass or wood in the body due to the accident, and a foreign substance that should be detected by the medical image in a case in which the foreign substance is swallowed. Examples of the substance that does not require a measure include a case in which the foreign substance embedded in the body of the patient PA for treatment of the patient PA is present with a normal position or function thereof, such as a pacemaker, an artificial joint, a stent, or an implant made of metallic or silicone resin that fixes a bone or the like, which is present with a normal position or function thereof. Note that in a case in which the foreign substance embedded in the body is present with an abnormal position or function thereof, the foreign substance may be the foreign substance that requires a measure. In addition, among the foreign substances present outside the body of the patient PA, examples of the foreign substance that requires a measure include an accessory, such as a necklace, of which the radiologist RT is not aware at the time of imaging, and a disposable body warmer, and examples of the foreign substance that does not require a measure include a foreign substance of which the type is clear and which does not affect the interpretation, such as a clothes that are clear from the shadow.

The presence or absence of the foreign substance image included in the medical image means whether or not the foreign substance image as described above is included in the medical image. In addition, the type of the foreign substance associated with the medical image is not limited to a type name of the foreign substance itself, but may be information regarding the type of the foreign substance. The correspondence information is information in which the medical image is associated in advance with the presence or absence of the foreign substance image included in the medical image in advance, or information in which the medical image is associated with the type of the foreign substance that forms the foreign substance image in a case in which the foreign substance image is present in the medical image.

For the medical image used in the correspondence information and the information on whether or not the foreign substance image is present in the medical image, the medical image acquired in the past, in which it is known whether or not the foreign substance image is present, and in a case in which the foreign substance image is present, the type of the foreign substance that forms the foreign substance image are known is used. In addition, the medical image that has not actually been acquired in the past may be used. For example, the correspondence information in which the image that has not actually been acquired and is generated by an assumed medical image by the image processing is associated with the corresponding foreign substance image and the information regarding the type of the foreign substance, or the correspondence information in which the image obtained by composing the actually acquired image is associated with the corresponding foreign substance image and the information regarding the type of the foreign substance may be used.

The correspondence information need only be the information in which the medical image is associated in advance with the presence or absence of the foreign substance image included in the medical image and the type of the foreign substance that forms the foreign substance image in a case in which the foreign substance image is present, a format, a generation method, or the like is not limited. The medical image is obtained by various modalities as described above. On the other hand, the presence or absence of the foreign substance image is the information of "presence" or "absence", and the type of the foreign substance is the information regarding the foreign substance. Therefore, the correspondence information can take various formats depending on the medical image and the information of the foreign substance. For example, the information obtained by creating the correspondence information in which the information regarding the medical image is associated with the "presence" or "absence" of the foreign substance image and the type name of the foreign substance in a table format may be used.

In addition, a learned model, which is created in advance, may be used as the correspondence information. Note that the learned model is model data in which the medical image is associated with the presence or absence of the foreign substance image included in the medical image and the type of the foreign substance by weighting by performing learning with machine learning on a plurality of the medical images, and is one type of the correspondence information. Note that the foreign substance image used in the correspondence information or the type of the foreign substance that forms the medical image may be plural. Therefore, for example, one medical image may be associated with the information regarding the types of a plurality of corresponding foreign substances. In addition, measure correspondence information including the information in which the medical image stored in the database described below is associated with measure information which is the information of a result of the determination or interpretation of the medical image by the medical staff may be used as the correspondence information.

As the correspondence information, a plurality of pieces of correspondence information may be used properly such that preferable foreign substance estimation information can be obtained depending on various conditions. Therefore, depending on various conditions, a plurality of tables may be created and used properly, or a plurality of the learned models may be created and used properly. For example, the preferable foreign substance estimation information may be obtained by properly using the tables or the learned models, which are the correspondence information, depending on the age of the patient PA. Note that the preferable foreign substance estimation information means that the information regarding the presence or absence of the foreign substance and the type of the foreign substance included in the foreign substance estimation information is close to the actuality, and the most preferable foreign substance estimation information means matches the actuality. Therefore, as the medical image and/or the correspondence information for generating the foreign substance estimation information, the information regarding the presence or absence of the foreign substance or the type of the foreign substance included in the foreign substance estimation information, which matches the actuality, is preferable.

As shown in FIG. 4, correspondence information 66 is the information in which the medical image is associated with the presence or absence of the foreign substance image included in the medical image and a type of the foreign substance that forms the foreign substance image in a case in which the foreign substance image is present. In the correspondence information 66, for example, the medical image, the presence or absence of the foreign substance image, and the type of the foreign substance are associated with each other on one-to-one basis. In a case in which the medical image is a medical image 66a, the correspondence information 66 is, for example, the information associated with "absence" as the presence or absence of the foreign substance image. In addition, in a case of a medical image 66b, "presence" as the presence or absence of the foreign substance image and "metallic necklace" as the type of the foreign substance are associated, in a case of a medical image 66c, "presence" as the presence or absence of the foreign substance image and "implantable device, manufactured by ABC, model: X-111" as the type of the foreign substance are associated, in a case of a medical image 66d, "presence" as the presence or absence of the foreign substance image and "foreign substance in the esophagus, button battery" as the type of the foreign substance are associated, and in a case of a medical image 66e, "presence" as the presence or absence of the foreign substance image and "surgical residual foreign substance, gauze" as the type of the foreign substance are associated. Note that the medical image 66a, the medical image 66b, the medical image 66c, and the medical image 66d are the X-ray images acquired by the computed radiography, and the medical image 66e is the CT image acquired by the computed tomography.

A unit by which the correspondence information acquisition unit 62 acquires the correspondence information 66 is not limited. For example, the correspondence information 66 is stored in the storage device 16 or another storage device (not shown) in advance, and the correspondence information acquisition unit 62 acquires the correspondence information 66 stored in the storage device 16 or the other storage device.

The foreign substance estimation unit 63 generates foreign substance estimation information obtained by estimating the presence or absence of the foreign substance image included in the medical image and the type of the foreign substance that forms the foreign substance image in a case in which the foreign substance image is present based on the medical image and the correspondence information 66. As described above, the foreign substance estimation unit 63 is connected to the image acquisition unit 61 and receives the medical image acquired by the image acquisition unit 61. In addition, the foreign substance estimation unit 63 is connected to the correspondence information acquisition unit 62, and receives the correspondence information 66 acquired by the correspondence information acquisition unit 62. The foreign substance estimation unit 63 estimates whether or not the foreign substance image is present in the medical image received from the image acquisition unit 61 based on the medical image received from the image acquisition unit 61 and the correspondence information 66 received from the correspondence information acquisition unit 62, and in a case in which it is estimated that the foreign substance image is present, generates the foreign substance estimation information obtained by estimating the type of the foreign substance that forms the foreign substance image. The foreign substance estimation information may include information regarding the medical image including the foreign substance, for example, the patient data in addition to the information regarding the foreign substance, such as foreign substance estimation information. For example, each time the medical image is received, the foreign substance estimation unit 63 automatically generates the foreign substance estimation information as soon as it is received. The estimated type of the foreign substance is not limited to one, and a plurality of types of the foreign substance may be included. In addition, in a case in which the foreign substance estimation unit 63 generates the foreign substance estimation information, it may be generated after weighting each information of the medical image and/or the correspondence information 66 to be used.

As shown in FIG. 5, for example, in a case in which the foreign substance estimation information of the medical image 65 received from the image acquisition unit 61 is generated, the foreign substance estimation unit 63 generates foreign substance estimation information 67 obtained by estimating the foreign substance estimation information in which the presence or absence of the foreign substance image is "presence" and the type of the foreign substance is "metallic necklace" based on the medical image 65 and the correspondence information 66. The foreign substance estimation information 67 is transmitted to the notification control unit 64, and for example, the notification is given by displaying the foreign substance estimation information 67 on the display of the medical support device 10. The notification is given by the display by text "estimation" for indicating that it is the information regarding the estimated type of the foreign substance and by the display by text "metallic necklace" indicating the estimated type of the foreign substance.

Note that in a case in which the foreign substance image is present in the medical image, the correspondence information acquisition unit 62 may acquire the correspondence information in which a position of the foreign substance is associated in addition to the medical image and the type of the foreign substance that forms the foreign substance image. That is, the information on the type of the foreign substance may include positional information of the foreign substance. The position of the foreign substance is the positional information of the foreign substance including an absolute position of the foreign substance and/or a relative position of the foreign substance. Therefore, the foreign substance estimation unit 63 may generate the foreign substance estimation information obtained by estimating the position of the foreign substance based on the correspondence information in which the medical image is associated with the position of the foreign substance.

As shown in FIG. 6, correspondence information 71 is the information in which the medical image is associated with the presence or absence of the foreign substance image included in the medical image and the type of the foreign substance that forms the foreign substance image and/or the position of the foreign substance in a case in which the foreign substance image is present. In the correspondence information 71, the medical image, the presence or absence of the foreign substance image, the type of the foreign substance that forms the foreign substance image, and/or the position of the foreign substance are associated with each other on one-to-one basis. In the correspondence information 71, for example, in a case of a medical image 66b, "presence" as the presence or absence of the foreign substance image, "metallic necklace" as the type of the foreign substance, "neck, outside the body" as the position of the foreign substance are associated, in a case of a medical image 66c, "presence" as the presence or absence of the foreign substance image, "implantable device, manufactured by ABC, model: X-111" as the type of the foreign substance, "in front of the left shoulder, beneath the skin" as the position of the foreign substance are associated, in a case of a medical image 66d, "presence" as the presence or absence of the foreign substance image, "foreign substance in the esophagus, button battery" as the type of the foreign substance, "esophagus, center" as the position of the foreign substance are associated, and in a case of a medical image 66e, "presence" as the presence or absence of the foreign substance image, "surgical residual foreign substance, gauze" as the type of the foreign substance, "diaphragm, lower right" as the position of the foreign substance are associated.

The foreign substance estimation unit 63 generates foreign substance estimation information obtained by estimating the presence or absence of the foreign substance image included in the medical image, the type of the foreign substance that forms the foreign substance image, and/or the position of the foreign substance in a case in which the foreign substance image is present based on the medical image and the correspondence information 71. The foreign substance estimation unit 63 estimates whether or not the foreign substance image is present in the medical image received from the image acquisition unit 61 based on the medical image received from the image acquisition unit 61 and the correspondence information received from the correspondence information acquisition unit 53, and in a case in which it is estimated that the foreign substance image is present, generates the foreign substance estimation information obtained by estimating the type of the foreign substance that forms the foreign substance image and/or the position of the foreign substance.

As shown in FIG. 7, for example, in a case in which the foreign substance estimation information of the medical image 65 received from the image acquisition unit 61 is generated, the foreign substance estimation unit 63 generates foreign substance estimation information 72 obtained by estimating the foreign substance estimation information in which the presence or absence of the foreign substance image is "presence", the type of the foreign substance is "metallic necklace", and the position of the foreign substance is "neck, outside the body" based on the medical image 65 and the correspondence information 71. In FIG. 7, the foreign substance estimation information 72 shows an aspect in a case in which the notification is given by the display. The foreign substance estimation information 72 is transmitted to the notification control unit 64, and for example, the notification is given by displaying the foreign substance estimation information 72 on the display of the medical support device 10. The notification is given by the display by text "estimation" for indicating that it is the information regarding the estimated type of the foreign substance, by the display by text "metallic necklace" indicating the estimated type of the foreign substance, and by the display by text "neck, outside the body" indicating the estimated position of the foreign substance.

In addition, the foreign substance estimation unit 63 may impart an adaptation degree to each of the presence or absence of the foreign substance image, the type of the foreign substance that forms the foreign substance image, and/or the position of the foreign substance, and may generate the foreign substance estimation information obtained by estimating a result of the presence or absence of the foreign substance image to which the adaptation degree equal to or larger than a specific value is imparted, the type of the foreign substance, and/or the position of the foreign substance. The adaptation degree imparted by the foreign substance estimation unit 63 is a numerical value corresponding to a probability that the presence or absence of the foreign substance image, the type of the foreign substance, and/or the position of the foreign substance, which are estimated, coincide with the actuality in a case in which the foreign substance estimation unit 63 estimates the foreign substance based on the medical image and the correspondence information. An imparting method of the adaptation degree is not limited, and for example, the estimation may be made by imparting the adaptation degree to each of the presence or absence of the foreign substance image, the type of the foreign substance, and/or the position of the foreign substance by machine learning technique using the learned model as the correspondence information. Since the adaptation degree is imparted to each of the presence or absence of the foreign substance, the type of the foreign substance that forms the foreign substance image, and/or the position of the foreign substance, the foreign substance estimation information may be created depending on the adaptation degree. For example, the foreign substance estimation information in a case in which the adaptation degree is set to be equal to or larger than the specific value may be created. It is possible to optionally set the adaptation degree.

As shown in FIG. 8, the foreign substance estimation unit 63 generates an estimated foreign substance list 81 in which the type of the foreign substance to which the adaptation degree is imparted is estimated based on, for example, the medical image 65 received from the image acquisition unit 61 and the correspondence information 66 received from the correspondence information acquisition unit 62. In the correspondence information 66, a medical image 66f is associated with "presence" of the presence or absence of the foreign substance image and "foreign substance in the esophagus, button battery" as the type of the foreign substance, a medical image 66g is associated with "presence" of the presence or absence of the foreign substance image and "clothes, metallic button" as the type of the foreign substance. For example, in a case in which foreign substance estimation information 82 is generated under the condition that the adaptation degree is equal to or larger than 70% of the type of examination, the foreign substance estimation information 82 is generated by "foreign substance in the esophagus, button battery" having the adaptation degree of "90%" in the estimated foreign substance list 81. Note that, depending on the setting, the notification control unit 64 may give the notification of the generation of the estimated foreign substance list 81. As the notification, for example, the generated estimated foreign substance list 81 may be displayed on the display of the medical support device 10 as a candidate for the estimated foreign substance.

The notification control unit 64 controls the notification based on the foreign substance estimation information. The control of the notification means to execution of the notification by deciding the matters for executing the notification, such as the presence or absence of a notification with or without a notification, a notification content in a case of the notification, the number of notifications in a case of the notification, or the other party in a case of the notification. These matters can be changed by setting. The notification content in a case in which the notification is given can be information regarding the foreign substance, such as the presence or absence of the foreign substance, the type of the foreign substance, the position of the foreign substance, or the like.

In the present embodiment, the notification is given to the radiologist RT or the like who uses the medical support device 10 to determine the imaging failure of the medical image. A notification unit is not limited as long as it can recognize that the notification is given to the radiologist RT. The notification may be given by at least one of image display, sound output, or vibration generation. The notification by the image display is an image display including the text and/or the image. For example, in the case of the notification by the output device 12 of the medical support device 10, the notification is given to the radiologist RT by displaying text or image on the display. The notification by the sound output or the notification by the vibration generation means, for example, outputting the sound by using the output device 12 provided in the medical support device 10 which emits the sound, or generating the vibration by communicating with the medical support device 10 by using the small portable terminal (not shown) owned by the radiologist RT in a case in which the generated foreign substance estimation information includes the information that the foreign substance image is present.

In addition, it is preferable that the notification be given to a person other than the patient PA. This is because, for example, the notification is given to only a person other than the patient PA who is the target person of the radiography to prevent causing the anxiety of the patient PA in a case of imaging. For example, in a case of imaging, in a case in which preliminary imaging is performed for positioning the subject of the patient PA and the notification is given to the radiologist RT based on the foreign substance estimation information by the medical support device 10 in that case, the radiologist RT can perform imaging after taking the measure for the foreign substance based on the foreign substance estimation information without causing the anxiety of the patient PA. Therefore, for example, in a case of the notification by the sound output, the medical support device 10 or an earphone connected to the small portable terminal communicating with the medical support device 10 may be used to control the sound output.

Figure 9:
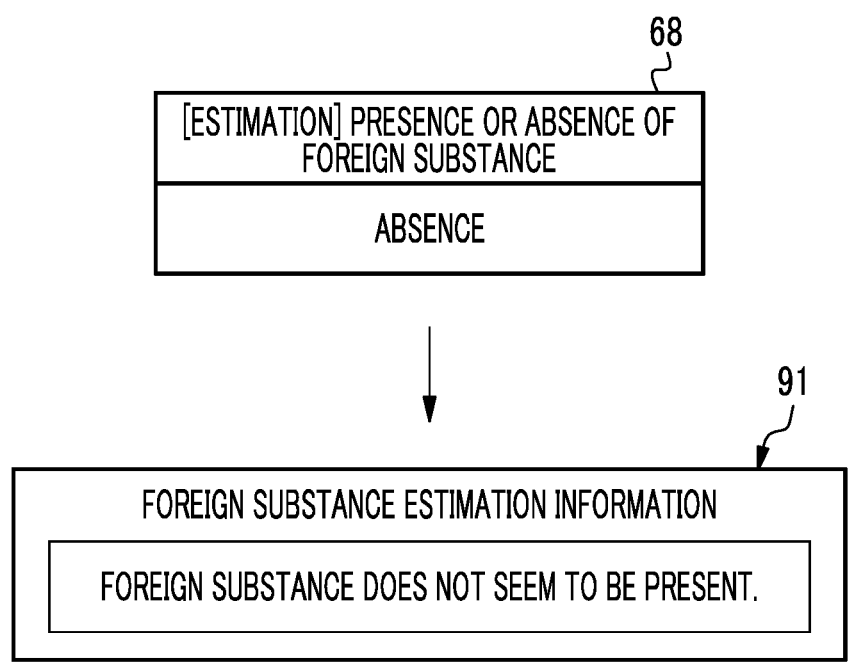
FIG. 9 is an explanatory diagram for describing a notification in a case in which it is estimated that a foreign substance image is not present.

The notification can be given, for example, as follows. For example, as shown in FIG. 9, in a case in which the foreign substance estimation information 68 has the information of "absence" as the presence or absence of the estimated foreign substance image, the notification control unit 64 performs a control of displaying a notification display 91 of which the notification content is decided to be displayed by the text "foreign substance estimation information" and "foreign substance does not seem to be present", for example, on the display of the medical support device 10.

Figure 10:
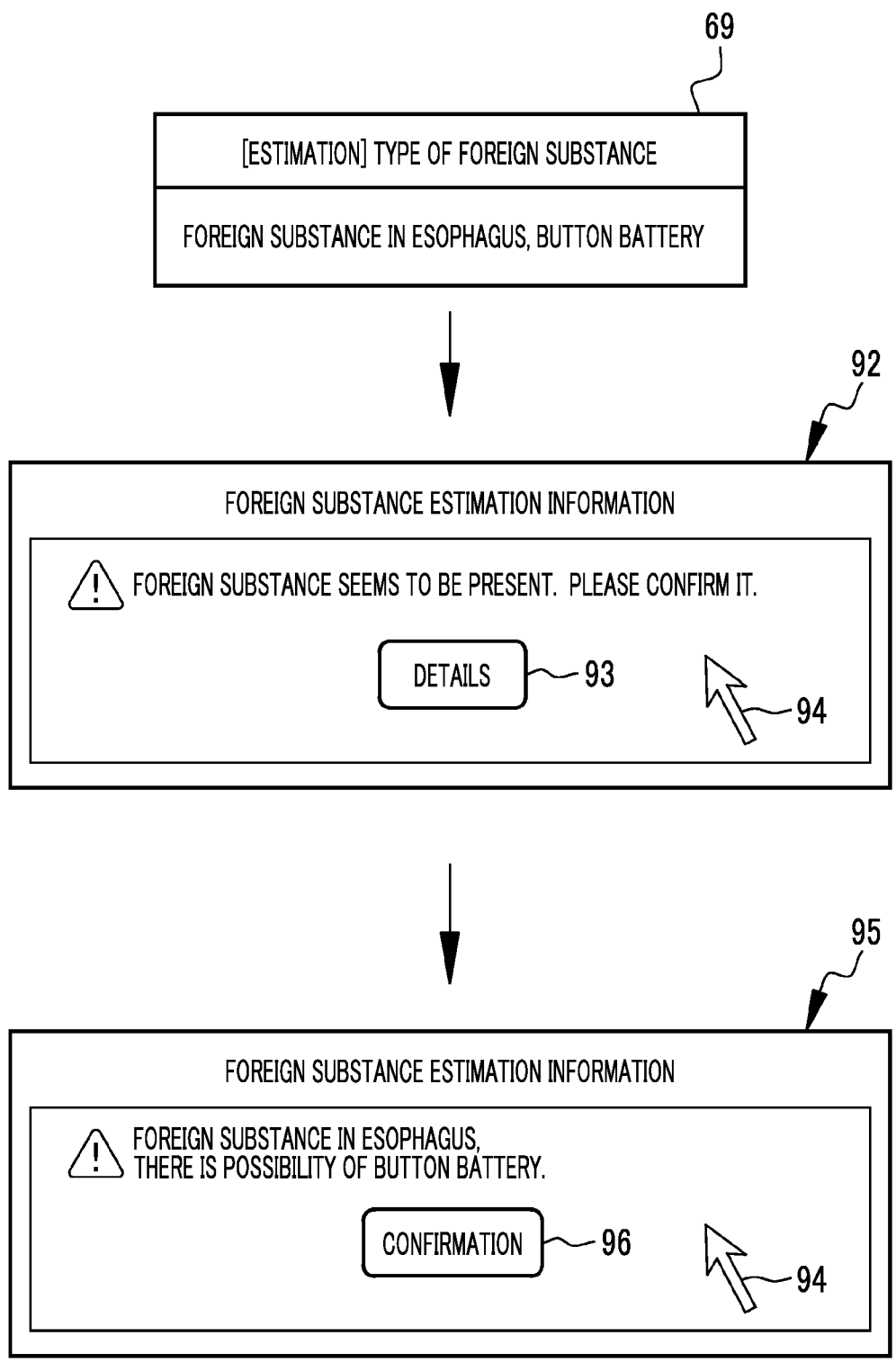
FIG. 10 is an explanatory diagram for describing a notification in a case in which it is estimated that the foreign substance image is present.

In addition, as shown in FIG. 10, in a case in which the foreign substance estimation information 69 has the information of "presence" as the presence or absence of the estimated foreign substance image and has the information of "foreign substance in the esophagus, button battery" as the estimated type of the foreign substance, the notification control unit 64 performs a control of displaying a notification display 92 of which the notification content is decided to be displayed by "foreign substance estimation information", an icon for warning, text "Foreign substance seems to be present. Please confirm it.", and a button 93 described as "details", for example, on the display of the medical support device 10. By designating and clicking the button 93 described as "details" in the notification display 92 with a cursor 94, a notification display 95 is displayed on the display. The notification display 95 is a display indicating detailed information regarding the foreign substance, and for example, the notification control unit 64 performs a control of displaying the notification display 95 of which the notification content is displayed by "foreign substance estimation information", and the icon for warning, text "Foreign substance in the esophagus, there is a possibility of the button battery.", and a button 96 described as "confirmation" on, for example, the display of the medical support device 10.

As described above, the medical support device 10 according to the embodiment of the present invention can support the medical staff including the radiologist RT or the interpreter such that the foreign substance image included in the medical image is not overlooked. For example, in a case in which the medical image is acquired, even in a case in which the foreign substance image of which the radiologist RT is not aware is included in the medical image, by generating the foreign substance estimation information and giving the notification controlled by the notification control unit 64 based on the foreign substance estimation information, it is possible to support the radiologist RT to more correctly determine the presence or absence of the foreign substance image included in the medical image and the type of the foreign substance that forms the foreign substance image. In addition, in a case in which the foreign substance estimation information includes the information regarding the position of the foreign substance, the radiologist RT can be notified of the information regarding the position of the foreign substance. Therefore, the radiologist RT can perform imaging after taking the measure for the foreign substance by the notification by the medical support device 10. Therefore, the radiologist RT can more reliably perform successful imaging in response to the imaging instruction, and can suppress the situation of re-imaging due to the imaging failure.

In addition, for example, in a case in which the interpreter interprets the medical image, for example, even in a case in which the foreign substance image of which the interpreter is not aware is included in the medical image, by giving the notification based on the foreign substance estimation information including the information regarding the type of the foreign substance that forms the foreign substance image, it is possible for the interpreter to be quickly aware of the foreign substance left in the body by the surgery. In addition, for example, it can be useful for learning of the interpreter who is not proficient in the interpretation to determine whether or not the foreign substance image is included in the medical image.

Figure 11:
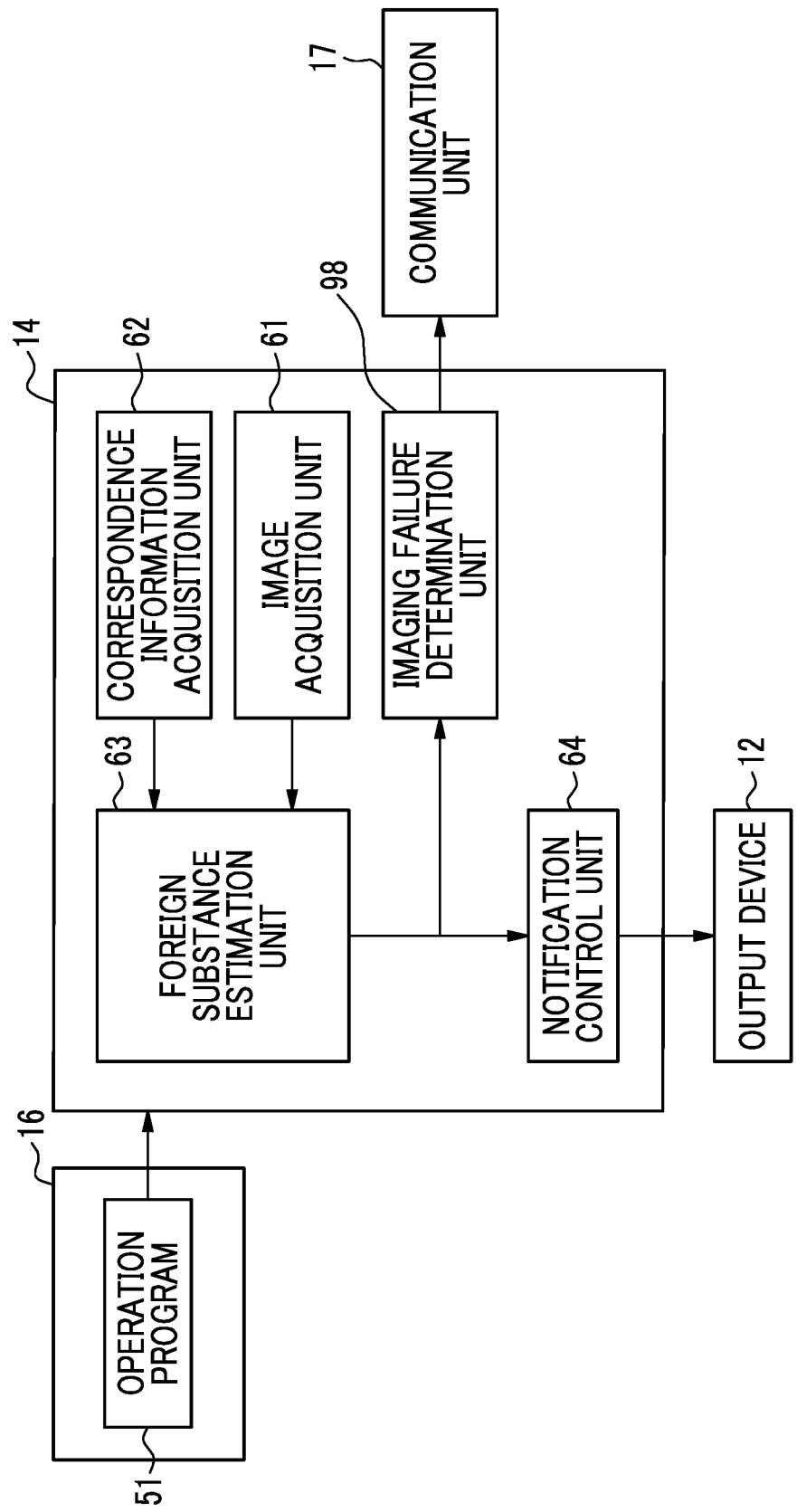

Note that, as shown in FIG. 11, the medical support device 10 may comprise the imaging failure determination unit 98 that generates imaging failure determination information obtained by determining whether or not the medical image is imaging-failed (hereinafter referred to as imaging failure determination) based on the foreign substance estimation information. The imaging failure determination unit 98 receives the foreign substance estimation information generated by the foreign substance estimation unit 63 for the medical image, and generates the imaging failure determination information which is a result of the imaging failure determination of the medical image based on the foreign substance estimation information. The imaging failure determination unit 98 comprises foreign substance-imaging failure correspondence information in which the type of the foreign substance is associated with the imaging failure. Therefore, the imaging failure determination unit 98 can generate the imaging failure determination information obtained by determining the imaging failure of the medical image based on the type of the foreign substance, which is the information regarding the foreign substance included in the foreign substance estimation information, and the foreign substance-imaging failure correspondence information.

The foreign substance-imaging failure correspondence information is a table in which the type of the foreign substance and the imaging failure are stored in advance in association with each other. For example, in the medical image, in a case in which the type of the foreign substance included in the foreign substance estimation information is "metallic necklace", the medical image is associated with "measure required", which is the imaging failure. "Measure required" means that there is a high possibility of the imaging failure and that measure, such as re-imaging, is necessary. It is preferable that the radiologist RT or the like be notified of the medical image that requires the measure of re-imaging. Note that the foreign substance-imaging failure correspondence information may be the learned model by machine learning.

In a case in which the imaging failure determination unit 98 determines that the imaging failure occurs, the notification is given to a person who decides the imaging failure, such as the radiologist RT. The notification need only be given to a person who determines the imaging failure, for example, by displaying on the display, generation of the sound, the light, or the vibration, or the like.

Depending on the type of the foreign substance, "measure required" is associated. The medical image having the type of the foreign substance to which "measure required" is not associated in the foreign substance estimation information has a low possibility of the imaging failure and has a low necessity of re-imaging, so that the imaging failure determination is not made, and the notification is not given.

In addition, it is preferable that the imaging failure determination unit 98 make the imaging failure determination on the foreign substance estimation information estimated in consideration of the adaptation degree. That is, in the estimated foreign substance list 81, the imaging failure determination may be made on the foreign substance having the highest adaptation degree, and the imaging failure determination may not be made on the foreign substance other than the foreign substance having the highest adaptation degree.

Specifically, in a case in which the foreign substance estimation information for the medical image includes "metallic necklace" as the type of the foreign substance having the highest adaptation degree, the imaging failure determination unit 98 determines the medical image to be "measure required" based on the foreign substance-imaging failure correspondence information. The medical image determined to be "measure required" by the imaging failure determination unit 98 is displayed with text "measure required" in a case of being displayed on the display. Therefore, the radiologist RT or the like can confirm the medical image and make the imaging failure determination after "measure required" is displayed on the display. A result of the imaging failure determination is transmitted to the RIS (not shown) or the like on the network 19 via the communication unit 17, and the re-imaging setting, the imaging menu setting, or the like is performed.

In addition, in some cases, the imaging failure determination may be made automatically. Automatic determination means that for the medical image in which the imaging failure, such as "measure required", is determined by the imaging failure determination unit 98, even in a case in which the imaging failure determination by the radiologist RT or the like is not made, the imaging failure is decided. In this case, the radiologist RT or the like is notified that the imaging failure is decided. In addition, even in a case in which the imaging failure is decided by the imaging failure determination unit 98, the subsequent re-imaging instructions and the like may be given in the same manner as the decision of the imaging failure by the radiologist RT, and these instructions may be automatically given.

Note that the medical support device may comprise the measure information acquisition unit that acquire the measure information regarding the measure corresponding to the medical image based on the notification, and the database that stores the measure correspondence information in which the medical image is associated with the measure information. The measure information is the information as the result of the determination or the interpretation of the medical image by the medical staff. The measure information includes, for example, information regarding the measure corresponding to the medical image, and the information regarding the measure includes, for example, information regarding the necessity of the measure and a content of the measure.

The measure information is decided by the radiologist RT, the doctor DR, or the like regarding the measure corresponding to the medical image. For example, in a case in which the notification that the medical image includes the foreign substance image is given by the notification by the medical support device and the radiologist RT confirms the shadow due to the foreign substance in the medical image, the radiologist RT decides the type of the foreign substance by referring to the information regarding the estimated type of the foreign substance, which is notified, and decides the measure for the medical image including the foreign substance image. Then, in a case in which the radiologist RT determines the imaging failure of the captured medical image and decides removal of the foreign substance and re-imaging, the matter that since correct diagnosis is impossible due to the foreign substance image, the imaging failure is determined and the matter that the foreign substance is the foreign substance that requires the measure and the foreign substance is to be removed at the time of re-imaging are decided as the measure information, and the decided contents are input to the medical support device as the measure information. On the other hand, in a case in which the radiologist RT decides the measure for the medical image including the foreign substance image that does not require re-imaging, the matter that the foreign substance image is the foreign substance that does not require the measure, and this medical image is not imaging-failed is decided as the measure information, and the decided contents are input to the medical support device as the measure information.

Figure 12:
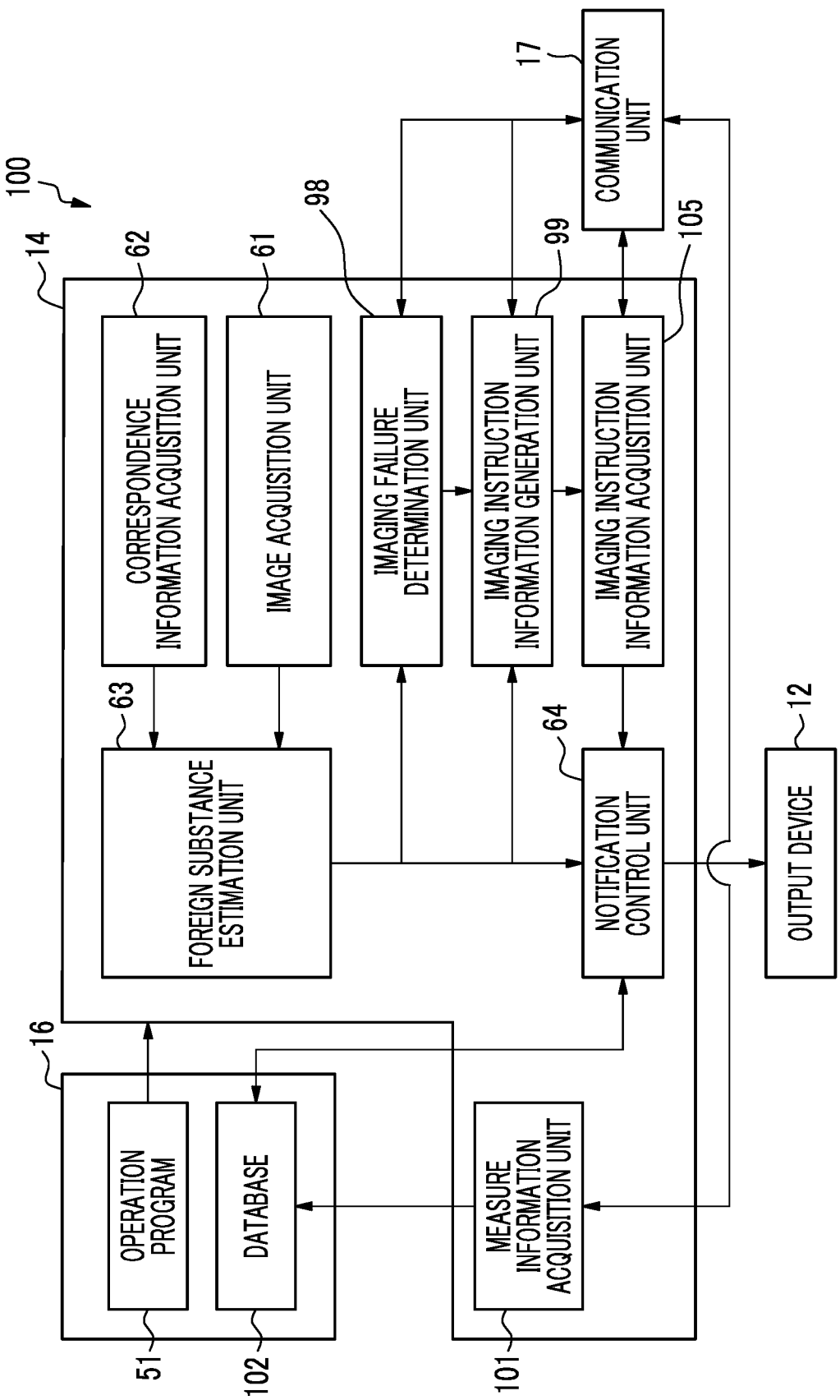

As shown in FIG. 12, a medical support device 100 comprises the measure information acquisition unit 101. The measure information acquisition unit 101 acquires the measure information. The measure information acquired by the measure information acquisition unit 101 is transmitted to database 102. The database 102 stores the measure correspondence information in which the medical image is associated with the measure information.

Figure 13:
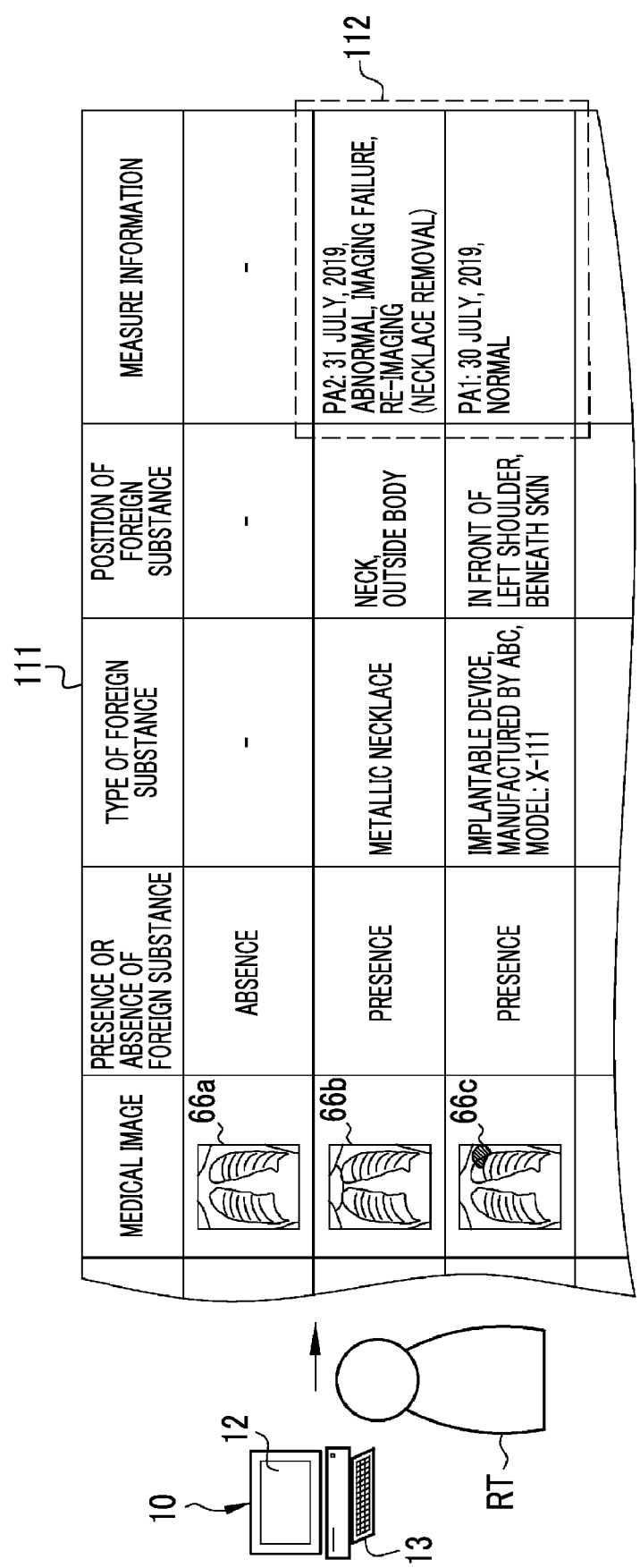
FIG. 13 is an explanatory diagram for describing measure information.

As shown in FIG. 13, the generated measure correspondence information 111 is, for example, information in which measure information 112 is further associated with the information included in the correspondence information in which the medical image is associated with the presence or absence of the foreign substance image. The measure information 112 is, for example, information regarding a result of the medical image 66b, which is estimated to include the foreign substance image and is notified, examined by the radiologist RT and determined including the content of the process. Therefore, for example, the medical image 66b in which it is estimated that the presence or absence of the foreign substance image is "presence", the type of the foreign substance is "metallic necklace", and the position of the foreign substance is "neck, outside the body" is examined by the radiologist RT, as a result, the measure information 112 is decided. The measure information 112 in this case is, for example, "abnormal, imaging failure, re-imaging (necklace removal)", and is the foreign substance that requires the measure. Therefore, as the measure, the medical image 66b is regarded as the imaging failure, and the imaging instruction for re-imaging is acquired by the RIS.

In addition, in a case of the medical image 66c which is estimated to include the foreign substance image and is notified, the medical image 66c in which it is estimated that the presence or absence of the foreign substance image is "presence", the type of the foreign substance is "implantable device" or the like, and the position of the foreign substance is "in front of the left shoulder, beneath the skin" is examined by the radiologist RT, as a result, the measure information 112 is decided to be "normal". In a case in which the measure information 112 includes "normal", no measure is required, the medical image 66c is not imaging-failed, and re-imaging is not performed. The measure information 112 is also acquired by the RIS.

Note that the measure information 112 may be information regarding the result of determination or interpretation of the medical image by the medical staff with reference to foreign substance estimation information, or may be information estimated as foreign substance estimation information. Therefore, the measure information 112 may include information different from the information estimated by the foreign substance estimation information. For example, even in a case in which the foreign substance estimation information is the medical image estimated to be "normal", in a case in which the interpreter decides recognition of the foreign substance image, the measure information 112 includes the information regarding the result of determination by the interpreter. The information regarding the result of determination by the interpreter may include at least one of the presence or absence of the foreign substance image, the type of the foreign substance, or the position of the foreign substance. Note that the measure correspondence information 111 may include the information, such as the patient information included in the imaging instruction information or the patient information included in the medical image, for example, in a case in which the medical image is acquired. Therefore, in FIG. 13, some patient information is also displayed in a measure information column for the convenience of the radiologist RT or the like, but a display method, such as which patient information is to be displayed, can be appropriately set.

The medical support device 100 comprises the measure information acquisition unit 101 and the database 102 that stores the measure correspondence information 111 in which the medical image is associated with the measure information, so that the determination related to the medical image can be made by the medical staff without leaving the determination related to the medical image to the device, and the measure correspondence information including the contents of determination of the medical staff can be effectively utilized for various scenes or uses.

Note that, in some cases, the measure information acquisition unit 101 may acquire the imaging failure determination information by the imaging failure determination unit 98 as the measure information from, for example, the imaging failure determination unit 98 or via the communication unit 17. In this case, the determination related to the medical image can be left to the device. In this case, the measure information acquisition unit 101 acquires the imaging failure determination information as the measure information, and automatically makes the determination related to the medical image in the same manner as a case in which the medical staff makes the determination related to the medical image.

In addition, the notification control unit 64 may control the notification based on the measure correspondence information. For example, in a case in which the foreign substance estimation information transmitted from the foreign substance estimation unit 63 includes the information regarding the medical image, such as the patient data, the notification control unit 64 controls the notification such that the notification is given by referring to the measure correspondence information regarding the medical image from the measure correspondence information stored in the database by using the information including the foreign substance estimation information and the like.

In addition, the medical support device 100 may comprise the imaging instruction information acquisition unit 105 (FIG. 12) that acquires the imaging instruction information for acquiring the medical image. Then, in a case in which the image acquisition unit 61 acquires the medical image including the subject image based on the imaging instruction information again, the notification control unit 64 may control the notification based on the imaging instruction information and/or the measure correspondence information regarding the medical image. The imaging instruction information acquisition unit 105 acquires the imaging instruction information from, for example, the RIS. The imaging instruction information is information regarding the imaging instruction transmitted from the doctor or the like to the image examination room 20 or the like. The imaging instruction is managed by the RIS, and the medical support device 10 acquires the imaging instruction information from the RIS that mutually communicates with medical support device 10. Therefore, the imaging instruction information includes the patient information and the like in addition to the information regarding the imaging instruction.

As shown in FIG. 14, in a case in which the imaging instruction information acquisition unit 105 acquires the matter that imaging of the patient PA2 is performed as the imaging instruction information, the notification control unit 64 acquires the measure information of the patient PA2 by using the measure correspondence information 111 stored in the database 102 by the patient data of the patient PA2 included in the imaging instruction information. The measure information includes the patient data, such as a name of the patient PA2, included in the imaging instruction information. Then, for example, the notification control unit 64 controls the notification based on whether or not the measure information under a specific condition, such as within the past one year, includes information to be noted such as "abnormal".

For example, for the patient PA2, re-imaging has been performed due to the medical image acquired including the foreign substance 32, which is the necklace, worn by the patient PA2 in a case of acquiring the medical image last time, and thus the information of "abnormal" is described in the measure information. Therefore, based on the imaging instruction information for imaging the patient PA2 and the measure information, in a case in which imaging is newly performed again on the same site of the patient PA2, the notification control unit 64 controls the notification such that the notification indicating that matter is given to the radiologist RT or the like before imaging. Therefore, based on the imaging instruction information and the measure information, the radiologist RT or the like can perform a warning WA in advance for a patient who tends to wear the foreign substance and perform imaging before imaging, resulting in the suppression of the imaging failure or re-imaging.

On the other hand, for example, for the patient PA1, in a case in which the foreign substance of the pacemaker is included in the medical image acquired last time, the radiologist RT or the like makes the determination, and there is the measure information that it is normal, the notification control unit 64 controls the notification such that the notification indicating that matter is given to the radiologist RT or the like before imaging in a case in which imaging is newly performed again on the same site of the patient PA1. Therefore, it is possible to handle the normal foreign substance in advance by using the imaging instruction information and the measure information, and for example, it is possible to prevent the foreign substance detected by the foreign substance estimation unit 63 from causing a decrease in efficiency of work, such as the determination of the medical image.

Note that, as shown in FIG. 12, the medical support device 100 may comprise the imaging instruction information generation unit 99, may transmit the imaging instruction information generated by the imaging instruction information generation unit 99 to the imaging instruction information acquisition unit 105, and to the RIS (not shown) via the communication unit 17 in the same manner. The imaging instruction information generation unit 99 generates the imaging instruction information based on the foreign substance estimation information, the measure information, and/or the imaging failure determination information. In some cases, the imaging instruction information generation unit 99 automatically generates details, such as execution of re-imaging and imaging menu, and transmits the details to the imaging instruction information acquisition unit 105 and the like to automatically set execution of re-imaging and the imaging menu.

In addition, the notification control unit 64 may perform the guide with respect to the patient having the subject based on the foreign substance estimation information. The guide is the notification that needs to be given to the patient in a case of imaging. The guide is to give the notification to the patient in a form that the patient can recognize a content of requesting the removal of the foreign substance, based on the foreign substance estimation information, in a case in which the patient wears the foreign substance that may cause the imaging failure in a case of imaging. For example, in a case in which the foreign substance estimation information 82 includes "metallic necklace", since there is a high possibility of the imaging failure and it is necessary to remove the foreign substance, the guide is performed with respect to the patient PA by the voice. Note that the guide includes the type of the foreign substance, and it is preferable to change the content of the guide including the content of the guide, the means of guide, and the number of times of guide depending on the type of the foreign substance or the necessity of removal.

In the guide with respect to the patient PA, which is the target of the radiography, the content of the guide can be an instruction for removing the foreign substance or the like. For example, with respect to the patient PA in the examination room 20b, the notification control unit 64 performs the guide of "please remove the necklace" in a case in which the foreign substance estimation information 82 includes "metallic necklace" and "please take off clothes" in a case in which the foreign substance estimation information includes "metallic button" by announcement by the voice or the image.

In a case in which the guide is performed with respect to the patient in addition to notifying the radiologist RT or the like, since it is possible to more reliably remove the foreign substance and smoothly perform imaging, it is preferable.

In addition, a medical support system comprising the medical support device 10 comprises the medical support device 10 described above. Moreover, as described above, the medical support system may comprise another device connected to the medical support device 10.

Figure 15:
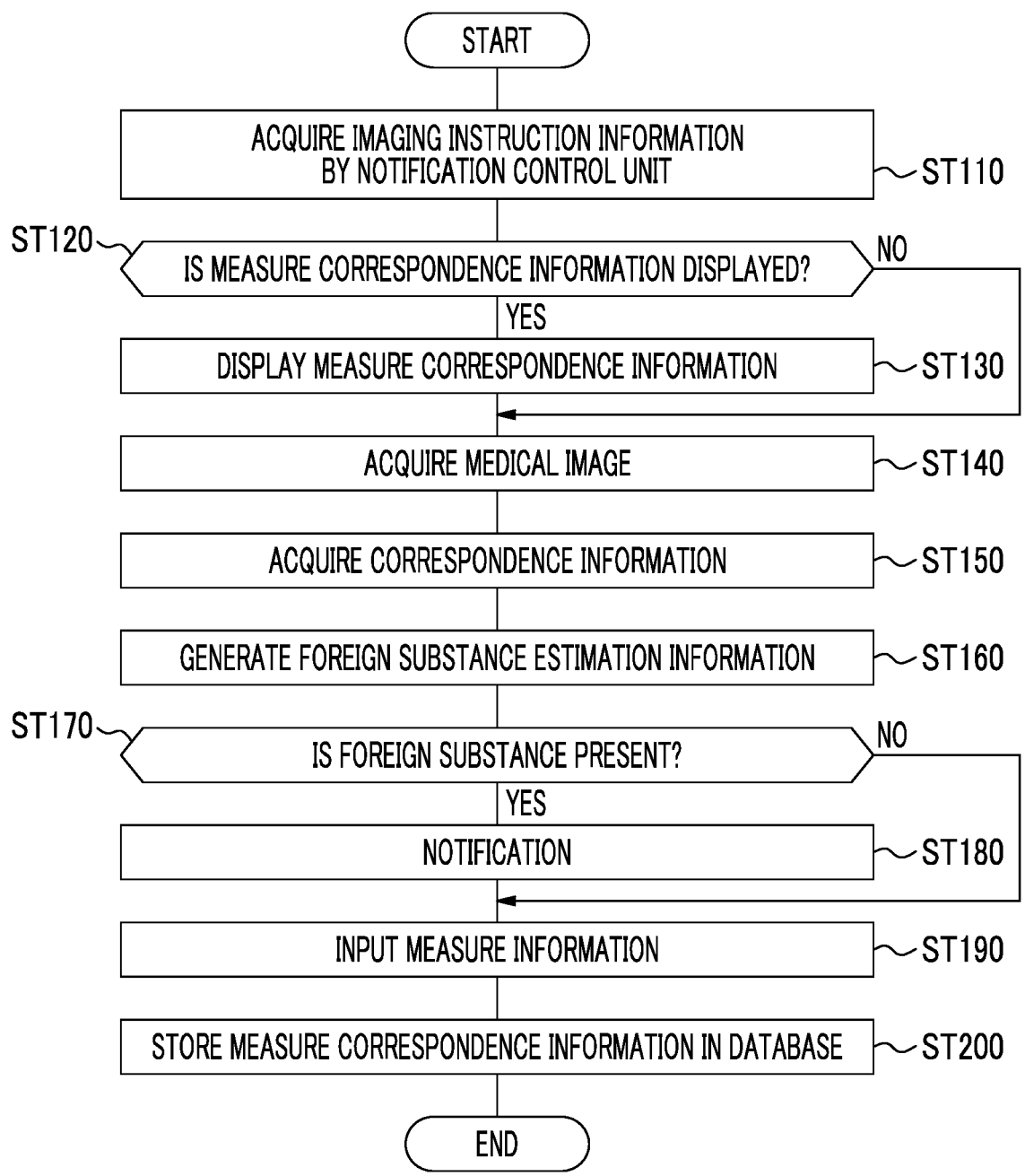
FIG. 15 is a flowchart showing a flow of estimation of the foreign substance.

Next, an operation of the configuration described above will be described with reference to the flowchart of FIG. 15. First, the notification control unit 64 acquires the imaging instruction information from the imaging instruction information acquisition unit 105 (step ST110). Next, the notification control unit 64 selects the measure correspondence information stored in the database 102 based on the imaging instruction information, performs a control whether or not the notification is given, in a case in which the notification of displaying the measure correspondence information is given (YES in step ST120), displays the measure correspondence information (step ST130), and in a case in which the control of not displaying the measure correspondence information is performed (NO in step ST120), does not display the measure correspondence information.

In a case in which the measure correspondence information is displayed, for example, according to the displayed measure correspondence information, the radiologist RT or the like removes the foreign substance in a case in which the foreign substance that the patient PA always has is present, or considers the matter that the pacemaker is present in a case in which the patient PA has the pacemaker, and the image acquisition unit 61 acquires the medical image for which it is desired to estimate whether or not the foreign substance image is present (step ST140). Next, the correspondence information acquisition unit 62 acquires the correspondence information in which the medical image that is known in advance to include the foreign substance image, the matter that the foreign substance image is included in the medical image, and/or the type of the foreign substance that forms the foreign substance image that is known are associated with each other in advance (step ST150).

The foreign substance estimation unit 63 creates the foreign substance estimation information obtained by estimating the presence or absence of the foreign substance image included in the acquired medical image, the type of the foreign substance, or the position of the foreign substance based on the acquired medical image and the correspondence information (step ST160). In a case in which the foreign substance estimation information includes the information that the foreign substance image is present (YES in step ST170), the notification control unit controls to perform the notification (step ST180). On the other hand, in a case in which the foreign substance estimation information includes the information that the foreign substance image is not present (NO in step ST170), the notification control unit controls the notification such that the notification is not performed.

Based on the notification, the measure correspondence information 111 is input by the radiologist RT or the like (step ST190). Then, the measure correspondence information 111 is stored in the database 102 (step ST200). As another modification example, the learned model may be recreated by using the measure correspondence information 111, and may be used as new correspondence information or a new foreign substance estimation unit.

In the embodiment described above, hardware structures of processing units which execute various processes, such as the image acquisition unit 61, the correspondence information acquisition unit 62, the foreign substance estimation unit 63, the notification control unit 64, the measure information acquisition unit 101, and the imaging instruction information acquisition unit 105, are various processors as follows. The various processors include a central processing unit (CPU), which is a general-purpose processor that executes software (program) and functions as various processing units, a programmable logic device (PLD) that is a processor of which a circuit configuration can be changed after manufacture, such as a field programmable gate array (FPGA), and a dedicated electric circuit (such as a graphical processing unit (GPU)), which is a processor having a circuit configuration that is designed for exclusive use in order to execute various processes.

One processing unit may be configured by one of these various processors, or a combination of two or more processors of the same type or different types (for example, a plurality of FPGAs, a combination of a CPU and a FPGA, or a combination of a GPU and a CPU). In addition, a plurality of the processing units may be configured by one processor. As an example of configuring the plurality of processing units with one processor, first, as represented by a computer, such as a client or a server, there is an aspect in which one processor is configured by a combination of one or more CPUs and the software and the processor functions as the plurality of processing units. Second, as represented by a system on chip (SoC), there is an aspect in which a processor is used in which the functions of the entire system including the plurality of processing units are realized by a single integrated circuit (IC) chip. In this way, the various processing units are configured by one or more of various processors described above as the hardware structures.

Moreover, the hardware structures of these various processors is, more specifically, an electric circuit (circuitry) having an aspect in which the circuit elements such as semiconductor elements are combined. Another aspect of the present invention relates to a medical support device including a processor that acquires a medical image including a subject image, acquires correspondence information in which the medical image is associated in advance with presence or absence of a foreign substance image included in the medical image and a type of a foreign substance that forms the foreign substance image in a case in which the foreign substance image is present, generates foreign substance estimation information obtained by estimating the presence or absence of the foreign substance image included in the medical image, the type of the foreign substance that forms the foreign substance image in a case in which the foreign substance image is present based on the medical image and the correspondence information, and controls a notification based on the foreign substance estimation information.

It is needless to say that the present invention is not limited to the embodiment described above, various configurations can be adopted as long as the configuration does not deviate from the gist of the present invention. Moreover, the present invention is applied to a storage medium that stores the program, in addition to the program.

EXPLANATION OF REFERENCES

10, 100: medical support device
12: output device
13: input device
14: CPU
15: memory
16: storage device
17: communication unit
18: data bus
19: network
20: image examination room
20*a*: operation room
20*b*: examination room
21: X-ray imaging apparatus
30: medical examination room
31, 32, 41: foreign substance
40: surgery room
42: surgery table 51: operation program
61: image acquisition unit
62: correspondence information acquisition unit
63: foreign substance estimation unit
64: notification control unit
65: medical image
66, 71: correspondence information
66a, 66b, 66c, 66d, 66e, 66f, 66g: medical image
67, 72, 82, 68, 69: foreign substance estimation information
81: estimated foreign substance list
91, 92, 95: notification display
93, 96: button
94: cursor
98: imaging failure determination unit
99: imaging instruction information generation unit
101: measure information acquisition unit
102: database
105: imaging instruction information acquisition unit
111: measure correspondence information
112: measure information
PA, PA1, PA2, PA3: patient
RT: radiologist
DR: doctor
WA: warning
ST110 to ST200: step

What is claimed is:

1. A medical support device comprising:
a processor configured to:
acquire a medical image including a subject image;
acquire correspondence information in which the medical image is associated in advance with presence or absence of a foreign substance image included in the medical image, a type of a foreign substance that forms the foreign substance image, and a position of the foreign substance in a case in which the foreign substance image is present, wherein the correspondence information is a learned model in which the medical image is associated with the presence or absence of the foreign substance image included in the medical image, the type of the foreign substance, and the position of the foreign substance by weighting and the learned model is created by performing learning with machine learning on a plurality of the medical images;
generate foreign substance estimation information obtained by estimating the presence or absence of the foreign substance image included in the medical image, the type of the foreign substance that forms the foreign substance image, and the position of the foreign substance in a case in which the foreign substance image is present based on the medical image and the correspondence information; and
control a notification based on the foreign substance estimation information.

2. The medical support device according to claim 1, wherein the processor is further configured to
acquire measure information regarding a measure corresponding to the medical image based on the notification, and
wherein the medical support device further includes a database that stores measure correspondence information in which the medical image is associated with the measure information.

3. The medical support device according to claim 2, wherein the processor is further configured to control the notification based on the measure correspondence information.

4. The medical support device according to claim 3, wherein the processor is further configured to:
acquire imaging instruction information for acquiring the medical image, and
control the notification based on the imaging instruction information and/or the measure correspondence information regarding the medical image in a case in which the medical image including the subject image based on the imaging instruction information is acquired again.

5. The medical support device according to claim 1, wherein the notification is performed by at least one of image display, sound output, or vibration generation.

6. The medical support device according to claim 1, wherein the notification is performed with respect to a person other than a patient having a subject that forms the subject image.

7. The medical support device according to claim 1, wherein the processor is further configured to perform a guide with respect to a patient having a subject based on the foreign substance estimation information.

8. The medical support device according to claim 7, wherein the guide includes the type of the foreign substance.

9. The medical support device according to claim 7, wherein the processor is further configured to change a content of the guide depending on the type of the foreign substance.

10. The medical support device according to claim 1, wherein the processor is further configured to generate imaging failure determination information obtained by determining whether or not the medical image is imaging-failed based on the foreign substance estimation information.

11. The medical support device according to claim 1, wherein the processor is further configured to generate imaging instruction information based on the foreign substance estimation information.

12. A medical support system comprising:
the medical support device according to claim 1.

13. The medical support system according to claim 12, further comprising:
a small portable terminal having a function of giving the notification,
wherein the processor is further configured to give the notification by the small portable terminal.

14. An operation method of a medical support device, the method comprising:
an image acquisition step of acquiring a medical image including a subject image;
an correspondence information acquisition step of acquiring correspondence information in which the medical image is associated in advance with presence or absence of a foreign substance image included in the medical image, a type of a foreign substance that forms the foreign substance image, and a position of the foreign substance in a case in which the foreign substance image is present, wherein the correspondence information is a learned model in which the medical image is associated with the presence or absence of the foreign substance image included in the medical image, the type of the foreign substance, and the position of the foreign substance by weighting and the learned model is created by performing learning with machine learning on a plurality of the medical images;
a foreign substance estimation information generation step of generating foreign substance estimation information obtained by estimating the presence or absence of the foreign substance image included in the medical image, and the type of the foreign substance that forms the foreign substance image, and the position of the foreign substance in a case in which the foreign substance image is present based on the medical image and the correspondence information; and a notification control step of controlling a notification based on the foreign substance estimation information.

15. A non-transitory computer readable medium for storing a computer-executable program causing a computer to function as the medical support device, the computer-executable program causing the computer to execute:

an image acquisition step of acquiring a medical image including a subject image;

an correspondence information acquisition step of acquiring correspondence information in which the medical image is associated in advance with presence or absence of a foreign substance image included in the medical image, a type of a foreign substance that forms the foreign substance image, and a position of the foreign substance in a case in which the foreign substance image is present, wherein the correspondence information is a learned model in which the medical image is associated with the presence or absence of the foreign substance image included in the medical image, the type of the foreign substance, and the position of the foreign substance by weighting and the learned model is created by performing learning with machine learning on a plurality of the medical images;

a foreign substance estimation information generation step of generating foreign substance estimation information obtained by estimating the presence or absence of the foreign substance image included in the medical image, and the type of the foreign substance that forms the foreign substance image, and the position of the foreign substance in a case in which the foreign substance image is present based on the medical image and the correspondence information; and a notification control step of controlling a notification based on the foreign substance estimation information.

* * * * *